US010376236B2

(12) United States Patent
Abe

(10) Patent No.: US 10,376,236 B2
(45) Date of Patent: Aug. 13, 2019

(54) ULTRASOUND DIAGNOSTIC APPARATUS, IMAGE PROCESSING APPARATUS, AND IMAGE PROCESSING METHOD

(71) Applicant: Canon Medical Systems Corporation, Otawara-shi (JP)

(72) Inventor: Yasuhiko Abe, Otawara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 300 days.

(21) Appl. No.: 14/717,646

(22) Filed: May 20, 2015

(65) Prior Publication Data

US 2015/0257731 A1 Sep. 17, 2015

Related U.S. Application Data

(63) Continuation of application No. PCT/JP2013/080813, filed on Nov. 14, 2013.

(30) Foreign Application Priority Data

Nov. 21, 2012 (JP) .................................. 2012-255579
Nov. 14, 2013 (JP) .................................. 2013-235938

(51) Int. Cl.
*A61B 8/08* (2006.01)
*G06T 7/246* (2017.01)

(52) U.S. Cl.
CPC .......... *A61B 8/0883* (2013.01); *A61B 8/5207* (2013.01); *G06T 7/246* (2017.01);
(Continued)

(58) Field of Classification Search
CPC .................................................. A61B 8/0883
See application file for complete search history.

(56) References Cited

U.S. PATENT DOCUMENTS 7,403,634 B2  7/2008 Nishiura
2003/0171668 A1  9/2003 Tsujino et al.
(Continued)

FOREIGN PATENT DOCUMENTS

JP  2002-306483 A  10/2002
JP  2003-250804 A  9/2003
(Continued)

OTHER PUBLICATIONS

International Search Report dated Dec. 10, 2013 for PCT/JP2013/080813 filed Nov. 14, 2013 with English Translation.
(Continued)

*Primary Examiner* — Rochelle D Turchen
(74) *Attorney, Agent, or Firm* — Oblon, McClelland, Maier & Neustadt, L.L.P.

(57) ABSTRACT

An ultrasound diagnostic apparatus according to an embodiment includes processing circuitry. The processing circuitry sets a ROI in ultrasound image data that corresponds to at least one temporal phase and is among moving image data of two-/three-dimensional ultrasound image data acquired while using a region containing a tissue in motion as an image taking target. The processing circuitry obtains first position information of an estimated ROI based on movement information and second position information of an estimated ROI based on information other than the movement information, in ultrasound image data corresponding to the other remaining temporal phases within an acquisition period of the moving image data. The processing circuitry tracks the ROI, by obtaining position information combining the first and second position information based on an index related to reliability of the movement information, as position information of the ROI.

14 Claims, 17 Drawing Sheets

(52) U.S. Cl.
CPC ............... *G06T 2207/10132* (2013.01); *G06T 2207/30048* (2013.01)

(56) References Cited

U.S. PATENT DOCUMENTS

| | | |
|---|---|---|
| 2010/0185090 A1 | 7/2010 | Suzuki et al. |
| 2010/0198072 A1 | 8/2010 | Abe et al. |
| 2012/0224759 A1 | 9/2012 | Masui et al. |
| 2013/0315456 A1* | 11/2013 | Marugame ............ G06T 7/0012 382/128 |

FOREIGN PATENT DOCUMENTS

| | | |
|---|---|---|
| JP | 4079690 B2 | 2/2008 |
| JP | 2008-073423 A | 4/2008 |
| WO | WO 2009/013871 A1 | 1/2009 |
| WO | WO 2011/052602 A1 | 5/2011 |

OTHER PUBLICATIONS

International Written Opinion dated Dec. 10, 2013 for PCT/JP2013/080813 filed Nov. 14, 2013.

Kiyotsugu Sekioka et al., "Assessment of Regional Intramyocardial Layer Function from Ultrasonic RF Echo Signals Using Hierarchical Correlation Method with Confidence", The Transactions of the Institute of Electronics, Information and Communication Engineers, Jan. 1, 2004, J87-DII(1), pp. 98-108.

\* cited by examiner

FIG.3
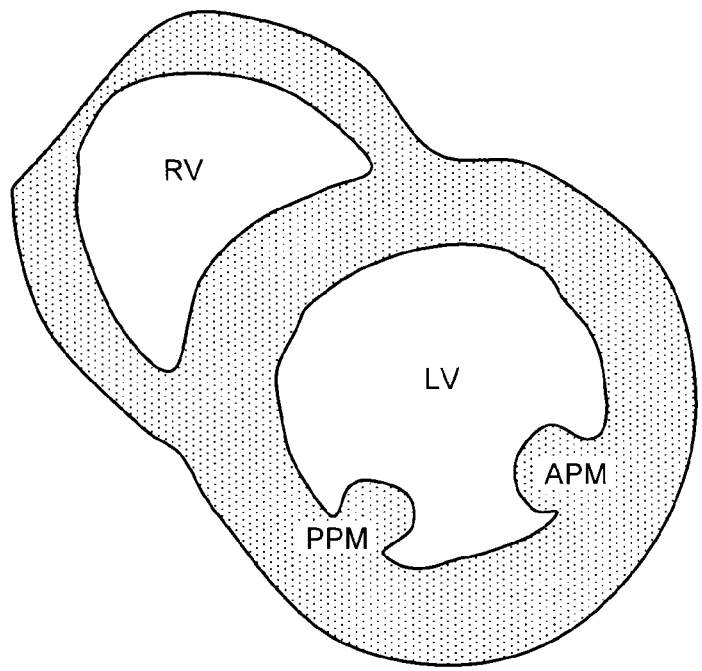
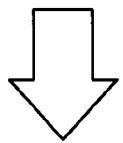
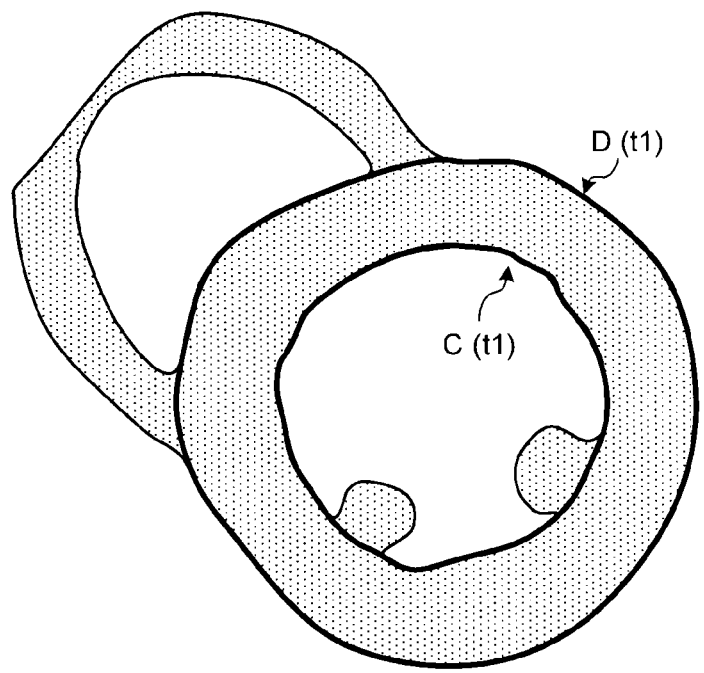

FIG.14
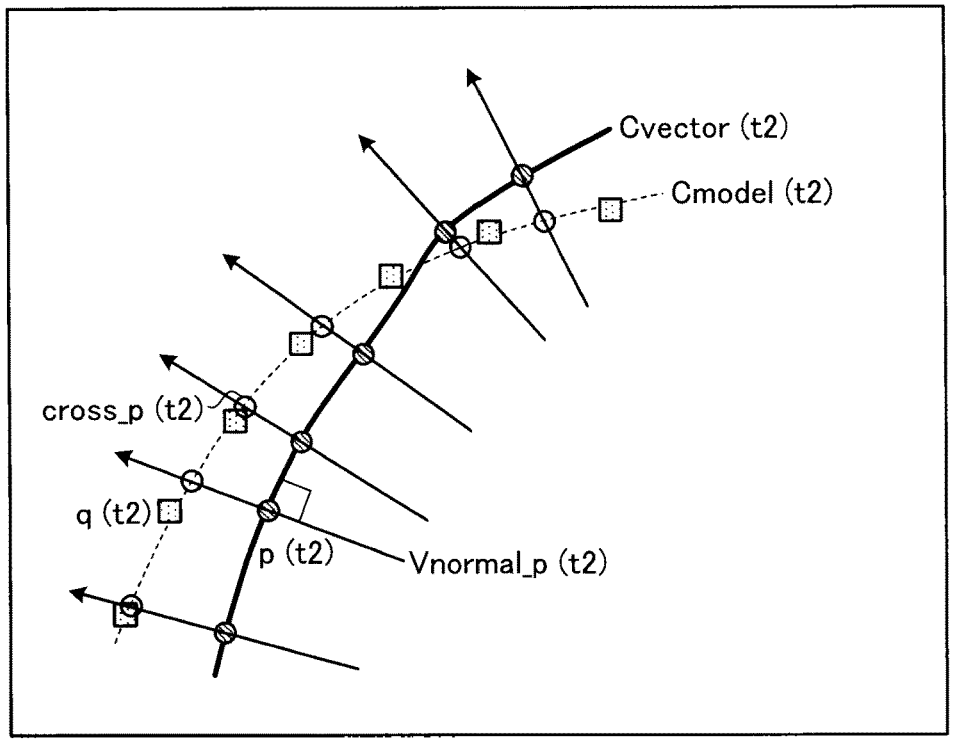
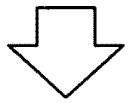
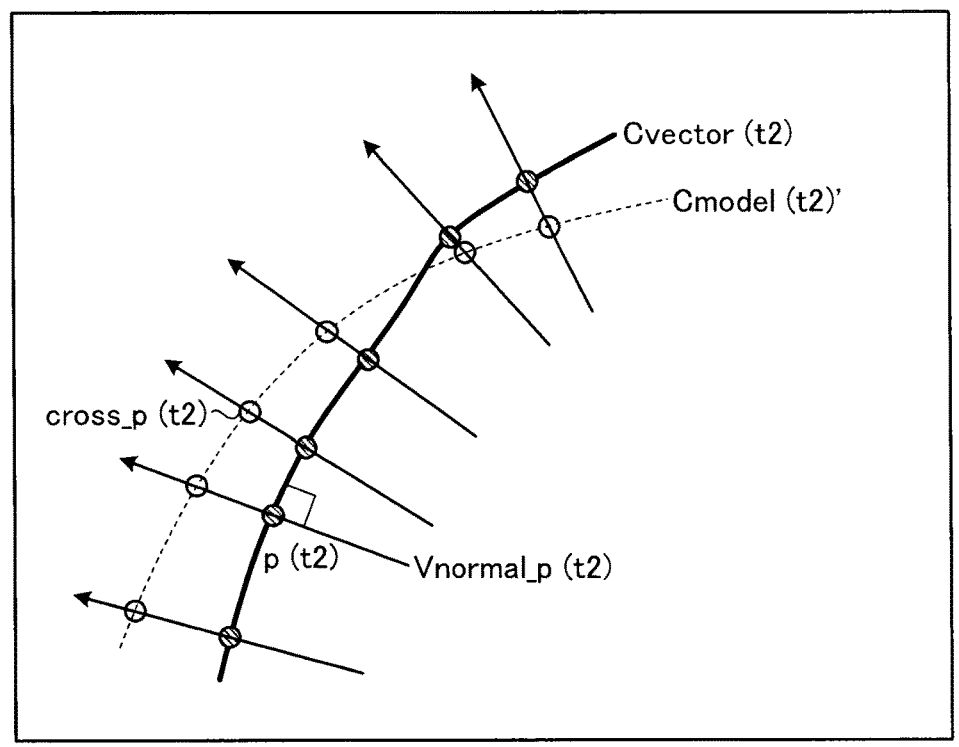

ULTRASOUND DIAGNOSTIC APPARATUS, IMAGE PROCESSING APPARATUS, AND IMAGE PROCESSING METHOD

CROSS-REFERENCE TO RELATED APPLICATIONS

This application is a continuation of PCT international application Ser. No. PCT/JP2013/080813 filed on Nov. 14, 2013 which designates the United States, incorporated herein by reference, and which claims the benefit of priority from Japanese Patent Application No. 2012-255579, filed on Nov. 21, 2012, and Japanese Patent Application No. 2013-235938, filed on Nov. 14, 2013, the entire contents of which are incorporated herein by reference.

FIELD

Embodiments described herein relate generally to an ultrasound diagnostic apparatus, an image processing apparatus, and an image processing method.

BACKGROUND

In recent years, cardiac wall motion analysis has been put to practical use by implementing two- or three-dimensional speckle tracking (ST) technology on moving images of ultrasound images. In a commonly-used ST process, contours of the inner and the outer layers of myocardia in a temporal phase at end-diastole (the first R-wave phase) or end-systole are provided as initial contour positions. Further, during the ST process, contour positions in all the necessary temporal phases are obtained by automatically tracking the initial contour positions in the remaining temporal phases, while using movement information (motion vectors) obtained by performing a local pattern matching process or by implementing an optical flow method. For this reason, to realize accurate tracking of the contour positions, it is essential to estimate the motion vectors accurately.

In an early diastolic (e') phase or a systolic peak (s') phase where the strain rate of the heart is large, however, extent of pattern change among frames or among volumes is large. For this reason, when using the speckle tracking process, it is difficult to accurately estimate the motion vectors if the frame rate or the volume rate is insufficient. In particular, when two-dimensional images are used, the tracked contour is influenced by a movement of going through a scanned cross-sectional plane (which is called a "through-plane" movement). Therefore, it is more difficult to accurately estimate the motion vectors, because the extent of pattern change among the frames is even larger.

Further, when the image quality of the moving images is low due to noise or artifacts, it is difficult to accurately estimate the motion vectors in such a part where the unnecessary components are mixed in. When it is not possible to accurately estimate the movement information for any of the various factors described above, a tracking failure occurs, and as a result, it is not possible to accurately perform the wall motion analysis.

To cope with this situation, various methods for performing an accurate tracking process have been proposed. However, none of the proposed methods is able to address all of the various factors described above. Thus, with the currently-used speckle tracking methods, it is not possible to accurately obtain contour tracking results in some situations. Further, the problems described above similarly occur when a region of interest is tracked by using moving images of medical images that are other than ultrasound images.

BRIEF DESCRIPTION OF THE DRAWINGS

FIG. 3 is a drawing of an example of initial contours set by an operator;

FIG. 6, FIG. 7, FIG. 8, FIG. 9, FIG. 10, FIG. 11, FIG. 12, FIG. 13A, FIG. 13B, FIG. 13C, FIG. 14, FIG. 15 and FIG. 16 are drawings for explaining the tracking unit according to the first embodiment;

DETAILED DESCRIPTION

An ultrasound diagnostic apparatus according to an embodiment includes processing circuitry. The processing circuitry is configured to set a two- or three-dimensional region of interest in ultrasound image data that corresponds to at least one temporal phase and is among pieces of moving image data of two- or three-dimensional ultrasound image data acquired while using a region containing a tissue in motion as an image taking target. The processing circuitry is configured to obtain first position information of a region estimated as the region of interest based on a movement information and second position information of a region estimated as the region of interest based on information other than the movement information, in pieces of ultrasound image data corresponding to remaining temporal phases other than said at least one temporal phase within a time period during which the pieces of moving image data were acquired. The processing circuitry is configured to track the region of interest, by obtaining position information resulting from combining the first position information with the second position information based on a reliability index related to reliability of the movement information, as position information of the region of interest.

Exemplary embodiments of an ultrasound diagnostic apparatus will be explained in detail below, with reference to the accompanying drawings.

Figure 1:
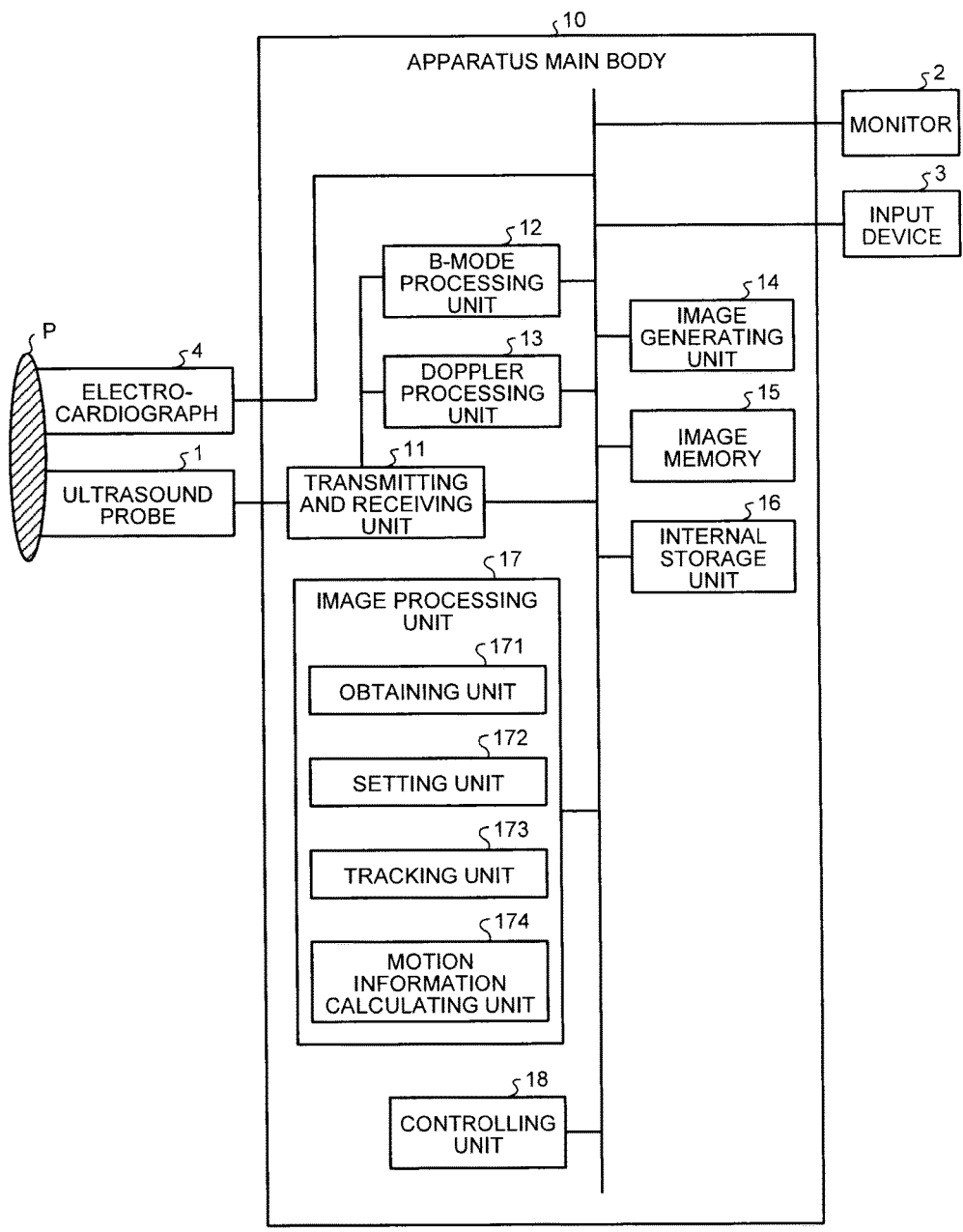
FIG. 1 is a block diagram of an exemplary configuration of an ultrasound diagnostic apparatus according to a first embodiment.

First, a configuration of an ultrasound diagnostic apparatus according to a first embodiment will be explained. FIG. 1 is a block diagram of an exemplary configuration of the ultrasound diagnostic apparatus according to the first embodiment. As illustrated in FIG. 1, the ultrasound diagnostic apparatus according to the first embodiment includes an ultrasound probe 1, a monitor 2, an input device 3, an electrocardiograph 4, and an apparatus main body 10.

The ultrasound probe 1 includes a plurality of piezoelectric transducer elements, which generate an ultrasound wave based on a drive signal supplied from a transmitting and receiving unit 11 included in the apparatus main body 10 explained later. Further, the ultrasound probe 1 receives a reflected wave from a subject P and converts the received reflected wave into an electric signal. Further, the ultrasound probe 1 includes a matching layer that is abutted on the piezoelectric transducer elements, as well as a backing member that prevents ultrasound waves from propagating rearward from the piezoelectric transducer elements. The ultrasound probe 1 is detachably connected to the apparatus main body 10.

When an ultrasound wave is transmitted from the ultrasound probe 1 to the subject P, the transmitted ultrasound wave is repeatedly reflected on discontinuous surfaces of acoustic impedances at a tissue in the body of the subject P and is received as a reflected-wave signal by the plurality of piezoelectric transducer elements included in the ultrasound probe 1. The amplitude of the received reflected-wave signal is dependent on the difference between the acoustic impedances on the discontinuous surface on which the ultrasound wave is reflected. When the transmitted ultrasound pulse is reflected on the discontinuous surface of a flowing bloodstream, a cardiac wall, and the like, the reflected-wave signal is, due to the Doppler effect, subject to a frequency shift, depending on a velocity component of the moving members with respect to the ultrasound wave transmission direction.

For example, according to the first embodiment, to scan the subject P two-dimensionally, a one-dimensional (1D) array probe in which the plurality of piezoelectric transducer elements are arranged in a row is connected to the apparatus main body 10, as the ultrasound probe 1. For example, the 1D array probe serving as the ultrasound probe 1 may be a sector probe that performs a sector scan, a convex probe that performs an offset sector scan, or a linear probe that performs a linear scan. Alternatively, in the first embodiment, for example, to scan the subject P three-dimensionally, a mechanical four-dimensional (4D) probe or a two-dimensional (2D) array probe may be connected to the apparatus main body 10, as the ultrasound probe 1. The mechanical 4D probe is able to perform a two-dimensional scan by employing a plurality of piezoelectric transducer elements arranged in a row like in a 1D array probe and is also able to perform a three-dimensional scan by causing the plurality of piezoelectric transducer elements to swing at a predetermined angle (a swinging angle). The 2D array probe is able to perform a three-dimensional scan by employing a plurality of piezoelectric transducer elements arranged in a matrix formation and is also able to perform a two-dimensional scan by transmitting ultrasound waves in a focused manner.

The input device 3 includes a mouse, a keyboard, a button, a panel switch, a touch command screen, a foot switch, a trackball, a joystick, and the like. The input device 3 receives various types of setting requests from an operator of the ultrasound diagnostic apparatus and transfers the received various types of setting requests to the apparatus main body 10. Setting information received from the operator by the input device 3 according to the first embodiment will be explained in detail later.

The monitor 2 displays a Graphical User Interface (GUI) used by the operator of the ultrasound diagnostic apparatus to input the various types of setting requests through the input device 3 and displays ultrasound image data and the like generated by the apparatus main body 10.

The electrocardiograph 4 obtains an electrocardiogram (ECG) of the subject P, as biological signals of the subject P on whom an ultrasound scan is performed. The electrocardiograph 4 transmits the obtained electrocardiogram to the apparatus main body 10.

The apparatus main body 10 is an apparatus that generates ultrasound image data based on the reflected-wave signal received by the ultrasound probe 1. The apparatus main body 10 illustrated in FIG. 1 is an apparatus that is able to generate two-dimensional ultrasound image data based on two-dimensional reflected-wave data received by the ultrasound probe 1. Further, the apparatus main body 10 illustrated in FIG. 1 is an apparatus that is able to generate three-dimensional ultrasound image data based on three-dimensional reflected-wave data received by the ultrasound probe 1. In the following sections, three-dimensional ultrasound image data may be referred to as "volume data".

As illustrated in FIG. 1, the apparatus main body 10 includes the transmitting and receiving unit 11, a B-mode processing unit 12, a Doppler processing unit 13, an image generating unit 14, an image memory 15, an internal storage unit 16, an image processing unit 17, and a controlling unit 18.

The transmitting and receiving unit 11 includes a pulse generator, a transmission delaying unit, a pulsar, and the like and supplies the drive signal to the ultrasound probe 1. The pulse generator repeatedly generates a rate pulse for forming a transmission ultrasound wave at a predetermined rate frequency. Further, the transmission delaying unit applies a delay period that is required to focus the ultrasound wave generated by the ultrasound probe 1 into the form of a beam and to determine transmission directionality and that corresponds to each of the piezoelectric transducer elements, to each of the rate pulses generated by the pulse generator. Further, the pulsar applies a drive signal (a drive pulse) to the ultrasound probe 1 with timing based on the rate pulses. In other words, the transmission delaying unit arbitrarily adjusts the transmission directions of the ultrasound waves transmitted from the piezoelectric transducer elements surface, by varying the delay periods applied to the rate pulses.

The transmitting and receiving unit 11 has a function to be able to instantly change the transmission frequency, the transmission drive voltage, and the like, for the purpose of executing a predetermined scanning sequence based on an instruction from the controlling unit 18 (explained later). In particular, the configuration to change the transmission drive voltage is realized by using a linear-amplifier-type transmitting circuit of which the value can be instantly switched or by using a mechanism configured to electrically switch among a plurality of power source units.

The transmitting and receiving unit 11 includes a pre-amplifier, an Analog/Digital (A/D) converter, a reception delaying unit, an adder, and the like and generates reflected-wave data by performing various types of processes on the reflected-wave signal received by the ultrasound probe 1. The pre-amplifier amplifies the reflected-wave signal for each of channels. The A/D converter applies an A/D conversion to the amplified reflected-wave signal. The reception delaying unit applies a delay period required to determine reception directionality to the result of the A/D conversion. The adder performs an adding process on the reflected-wave signals processed by the reception delaying unit so as to generate the reflected-wave data. As a result of the adding process performed by the adder, reflected components from the direction corresponding to the reception directionality of the reflected-wave signals are emphasized. A comprehensive beam used in an ultrasound transmission/reception is thus formed according to the reception directionality and the transmission directionality.

When a two-dimensional scan is performed on the subject P, the transmitting and receiving unit 11 causes the ultrasound probe 1 to transmit two-dimensional ultrasound beams. The transmitting and receiving unit 11 then generates two-dimensional reflected-wave data from the two-dimensional reflected-wave signals received by the ultrasound probe 1. When a three-dimensional scan is performed on the subject P, the transmitting and receiving unit 11 causes the ultrasound probe 1 to transmit three-dimensional ultrasound beams. The transmitting and receiving unit 11 then generates three-dimensional reflected-wave data from the three-dimensional reflected-wave signals received by the ultrasound probe 1.

Output signals from the transmitting and receiving unit 11 can be in a form selected from various forms. For example, the output signals may be in the form of signals called Radio Frequency (RF) signals that contain phase information or may be in the form of amplitude information obtained after an envelope detection process.

The B-mode processing unit 12 receives the reflected-wave data from the transmitting and receiving unit 11 and generates data (B-mode data) in which the strength of each signal is expressed by a degree of brightness, by performing a logarithmic amplification, an envelope detection process, and the like on the received reflected-wave data.

The Doppler processing unit 13 performs frequency analysis on velocity information received from the transmitting and receiving unit, to extract bloodstream, tissues, and contrast-agent echo components by the Doppler effect, and to further generate data (Doppler data) obtained by extracting moving member information such as a velocity, a variance, a power for a plurality of points.

The B-mode processing unit 12 and the Doppler processing unit 13 according to the first embodiment are able to process both two-dimensional reflected-wave data and three-dimensional reflected-wave data. In other words, the B-mode processing unit 12 is able to generate two-dimensional B-mode data from two-dimensional reflected-wave data and to generate three-dimensional B-mode data from three-dimensional reflected-wave data. The Doppler processing unit 13 is able to generate two-dimensional Doppler data from two-dimensional reflected-wave data and to generate three-dimensional Doppler data from three-dimensional reflected-wave data.

The image generating unit 14 generates ultrasound image data from the data generated by the B-mode processing unit 12 and the Doppler processing unit 13. In other words, from the two-dimensional B-mode data generated by the B-mode processing unit 12, the image generating unit 14 generates two-dimensional B-mode image data in which the strength of the reflected wave is expressed by a degree of brightness. Further, from the two-dimensional Doppler data generated by the Doppler processing unit 13, the image generating unit 14 generates two-dimensional Doppler image data expressing moving member information. The two-dimensional Doppler image data is velocity image data, variance image data, power image data, or image data combining these types of image data. Further, from the Doppler data generated by the Doppler processing unit 13, the image generating unit 14 is also able to generate a Doppler waveform in which the velocity information of the bloodstream and/or the tissues is plotted in chronological order.

In this situation, generally speaking, the image generating unit 14 converts (by performing a scan convert process) a scanning line signal sequence from an ultrasound scan into a scanning line signal sequence in a video format used by, for example, television and generates display-purpose ultrasound image data. Specifically, the image generating unit 14 generates the display-purpose ultrasound image data by performing a coordinate transformation process compliant with the ultrasound scanning mode by the ultrasound probe 1. Further, as various types of image processes other than the scan convert process, the image generating unit 14 performs, for example, an image process (a smoothing process) to regenerate a brightness-average image or an image process (an edge enhancement process) using a differential filter within images, while using a plurality of image frames obtained after the scan convert process is performed. Further, the image generating unit 14 superimposes text information of various parameters, scale marks, body marks, and the like on the ultrasound image data.

In other words, the B-mode data and the Doppler data are the ultrasound image data before the scan convert process is performed. The data generated by the image generating unit 14 is the display-purpose ultrasound image data obtained after the scan convert process is performed. The B-mode data and the Doppler data may also be referred to as raw data.

Further, the image generating unit 14 generates three-dimensional B-mode image data by performing a coordinate transformation process on the three-dimensional B-mode data generated by the B-mode processing unit 12. Further, the image generating unit 14 generates three-dimensional Doppler image data by performing a coordinate transformation process on the three-dimensional Doppler data generated by the Doppler processing unit 13. In other words, the image generating unit 14 generates "the three-dimensional B-mode image data or the three-dimensional Doppler image data" as "three-dimensional ultrasound image data (volume data)".

Further, the image generating unit 14 performs a rendering process on the volume data, to generate various types of two-dimensional image data used for displaying the volume data on the monitor 2. Examples of the rendering process performed by the image generating unit 14 include a process to generate Multi Planar Reconstruction (MPR) image data from the volume data by implementing an MPR method. Other examples of the rendering process performed by the image generating unit 14 include a process to apply a "curved MPR" to the volume data and a process to apply a "maximum intensity projection" to the volume data. Another example of the rendering process performed by the image generating unit 14 is a Volume Rendering (VR) process.

The image memory 15 is a memory that stores therein the display-purpose image data generated by the image generating unit 14. Further, the image memory 15 is also able to store therein the data generated by the B-mode processing unit 12 or the Doppler processing unit 13. After a diagnosis process, for example, the operator is able to invoke the B-mode data or the Doppler data stored in the image memory 15. The invoked data is served as the display-purpose ultrasound image data by the image generating unit 14.

The image generating unit 14 stores the ultrasound image data and the time at which the ultrasound scan was performed to generate the ultrasound image data into the image memory 15, in such a manner that the ultrasound image data and the time are kept in correspondence with the electrocardiogram transmitted from the electrocardiograph 4. By referring to the data stored in the image memory 15, the image processing unit 17 and the controlling unit 18 (explained later) are able to obtain cardiac phases during the ultrasound scan performed to generate the ultrasound image data.

The internal storage unit 16 stores therein various types of data such as a control program (hereinafter, "control program") to execute ultrasound transmissions and receptions, image process, and display process, as well as diagnosis information (e.g., patients' IDs, doctors' observations), diagnosis protocols, and various types of body marks. Further, the internal storage unit 16 may be used, as necessary, for storing therein any of the image data stored in the image memory 15. Further, it is possible to transfer the data stored in the internal storage unit 16 to an external apparatus via an interface (not shown). Examples of the external apparatus include a high-performance workstation used for processing images, a personal computer (PC) used by a doctor who performs an image diagnosis, a storage medium such as a compact disk (CD) or a digital versatile disk (DVD), a printer, and the like.

The image processing unit 17 is installed in the apparatus main body 10 for performing a Computer-Aided Diagnosis (CAD). The image processing unit 17 obtains the ultrasound image data stored in the image memory 15 and performs image processing to support a diagnosis. Further, the image processing unit 17 stores results of the image processing into the image memory 15 or the internal storage unit 16.

Specifically, the image processing unit 17 according to the first embodiment is installed for providing motion information of a tissue in motion. The tissue in motion described above refers to a tissue in periodic motion such as the heart. As illustrated in FIG. 1, the image processing unit 17 according to the first embodiment includes an obtaining unit 171, a setting unit 172, a tracking unit 173, and a motion information calculating unit 174. Processes performed by the image processing unit 17 will be explained in detail later.

The controlling unit 18 controls the entire processes performed by the ultrasound diagnostic apparatus. Specifically, based on the various types of setting requests input by the operator by the input device 3 and various types of control programs and various types of data invoked from the internal storage unit 16, the controlling unit 18 controls processes performed by the transmitting and receiving unit 11, the B-mode processing unit 12, the Doppler processing unit 13, the image generating unit 14, and the image processing unit 17. Further, the controlling unit 18 exercises control so that the monitor 2 displays the display-purpose ultrasound image data stored in the image memory 15 and the internal storage unit 16. Further, the controlling unit 18 exercises control so that the processing results obtained by the image processing unit 17 are displayed on the monitor 2 or output to an external apparatus.

An overall configuration of the ultrasound diagnostic apparatus according to the first embodiment has thus been explained. The image processing unit 17 included in the ultrasound diagnostic apparatus according to the first embodiment structured as described above tracks a region of interest in a group of ultrasound data (moving image data of ultrasound image data) in chronological order, so as to provide motion information of a tissue in motion (e.g., a tissue in periodic motion). In an example, to provide motion information of a cardiac wall that is in periodic motion, the image processing unit 17 according to the first embodiment tracks a contour of the inner layer of myocardia and a contour of the outer layer of myocardia in moving image data of ultrasound image data.

The moving image data that is served as a processing target of the image processing unit 17 may be a group of two-dimensional ultrasound image data or a group of three-dimensional ultrasound image data.

First, the obtaining unit 171 illustrated in FIG. 1 obtains moving image data of two- or three-dimensional ultrasound image data acquired while using a region containing a tissue in motion as an image taking target. Specifically, in the first embodiment, the moving image data is the two- or three-dimensional ultrasound image data that corresponds to a time period of at least one cyclic period and that was acquired while using a tissue in periodic motion, i.e., the tissue in motion, as the image taking target. In other words, the obtaining unit 171 obtains the moving image data of the two- or three-dimensional ultrasound image data that corresponds to a time period of at least one cyclic period and that was acquired while using the region containing the tissue in periodic motion as the image taking target. For example, the operator performs a two-dimensional scan or a three-dimensional scan on a region that contains the heart of the subject P by using a sector probe, so as to perform an image taking process to acquire moving image data of two- or three-dimensional ultrasound image data that renders myocardia. For example, the moving image data is a group of ultrasound image data acquired in a B-mode. Accordingly, the image generating unit 14 generates moving image data of the myocardia and stores the generated moving image data into the image memory 15.

In the following sections, an example will be explained in which the operator performs a two-dimensional scan on a left ventricular short-axis cross-sectional plane at a papillary muscle level, so as to acquire pieces of moving image data of two-dimensional ultrasound image data that correspond to a plurality of heartbeats. The ultrasound image data of the left ventricular short-axis cross-sectional plane at the papillary muscle level renders a part of a short-axis plane of the right ventricle (RV) and the entirety of a short-axis plane of the left ventricle (LV). Further, the ultrasound image data of the left ventricular short-axis cross-sectional plane at the papillary muscle level renders the anterolateral papillary muscle (APM) and the posteromedial papillary muscle (PPM) in the left ventricle.

Further, for example, the operator sets a one-heartbeat period from the first end diastole (ED) to the next end diastole, as a time period serving as a target of the tracking process. In the following explanation, the temporal phase of the first end diastole will be referred to as "ED0", whereas the temporal phase of the next end diastole will be referred to as "ED1". Thus, "ED0" denotes a tracking start temporal phase, whereas "ED1" denotes a tracking end temporal phase.

Figure 2:
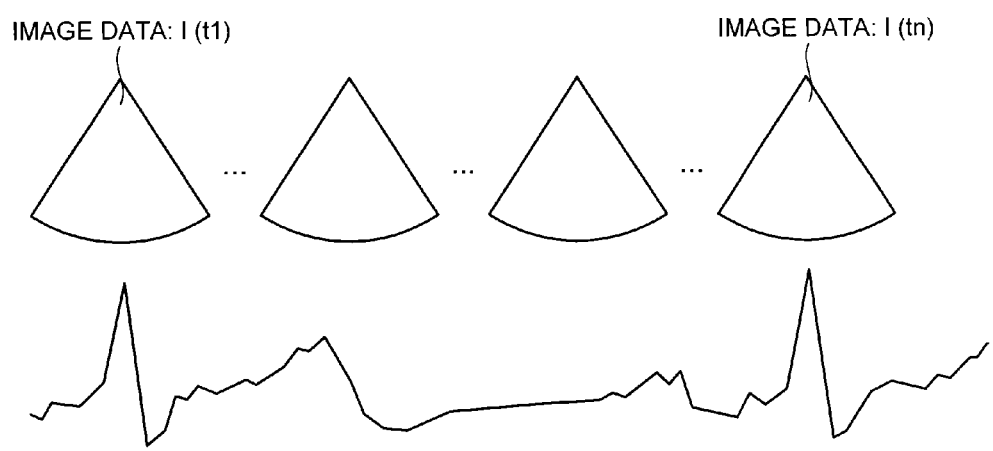
FIG. 2 is a drawing of an example of moving image data obtained by an obtaining unit.

The obtaining unit 171 obtains moving image data corresponding to the one-heartbeat period (t=ED0 to Ed1) set by the operator, from the image memory 15. FIG. 2 is a drawing of an example of the moving image data obtained by the obtaining unit. For example, as illustrated in FIG. 2, the obtaining unit 171 obtains, from the image memory 15, pieces of image data from a piece of image data "I(t1)" at "temporal phase: t1=E0" to a piece of image data "I(tn)" at "temporal phase: tn=E1", as two-dimensional moving image data corresponding to the one-heartbeat period (t=ED0 to ED1). The first embodiment is also applicable to a situation where the obtaining unit 171 obtains moving image data of three-dimensional ultrasound image data. Further, the first embodiment is also applicable to a situation where a two-heartbeat period or a three-heartbeat period is set as a time period that serves as a target of the tracking process.

The setting unit 172 illustrated in FIG. 1 sets a two- or three-dimensional region of interest in ultrasound image data that corresponds to at least one temporal phase among the pieces of moving image data obtained by the obtaining unit 171. If the moving image data is a group of two-dimensional ultrasound image data, the setting unit 172 sets a two-dimensional region of interest. In contrast, if the moving image data is a group of three-dimensional ultrasound image data, the setting unit 172 sets a two- or three-dimensional region of interest.

Further, in the first embodiment in which the operator is to be provided with the motion information of the cardiac wall that is in periodic motion, the region of interest is a contour of the inner layer of the left ventricle (hereinafter, "left ventricular inner layer") and a contour of the outer layer of the myocardia (hereinafter, "myocardial outer layer"). In the first embodiment, the setting unit 172 sets the region of interest based on information set by the operator. FIG. 3 is a drawing of an example of initial contours set by the operator.

For example, by using the input device 3, the operator requests to display the image data "I(t1)" at the tracking start temporal phase "t1=E0". The monitor 2 displays the image data "I(t1)" under the control of the controlling unit 18. The operator refers to the image data "I(t1)" illustrated in the top section of FIG. 3 and traces the position of the contour of the left ventricular inner layer. In addition, the operator refers to the image data "I(t1)" illustrated in the top section of FIG. 3 and traces the position of the contour of the myocardial outer layer. Accordingly, as illustrated in the bottom section of FIG. 3, the setting unit 172 sets the position of the contour of the left ventricular inner layer traced by the operator as an initial contour position "C(t1)" of the left ventricular inner layer. In addition, as illustrated in the bottom section of FIG. 3, the setting unit 172 sets the position of the contour of the myocardial outer layer traced by the operator as an initial contour position "D(t1)" of the myocardial outer layer. In FIG. 3, the contour lines traced by the operator are indicated with bold curves. In this situation, the contour position of the myocardial outer layer may automatically be rendered in a position that is distant from the position of the endocardium with a predetermined thickness (with a predetermined distance).

The first embodiment may also be configured so that the position of the contour of a middle layer of the myocardia is set as an initial contour position. Further, the first embodiment is not limited to the example in which the initial contour position manually set by the operator is used. The first embodiment may be configured so that the setting unit 172 automatically sets an initial contour position based on brightness levels of the ultrasound image data or the like.

Further, the tracking unit 173 illustrated in FIG. 1 tracks the region of interest in the pieces of ultrasound image data corresponding to remaining temporal phases other than the temporal phase in which the initial region of interest was set, within the time period during which the pieces of moving image data were acquired. Specifically, the tracking unit 173 tracks the region of interest in the pieces of ultrasound image data corresponding to the remaining temporal phases other than the temporal phase in which the initial region of interest was set, within the time period serving as the tracking target. For example, the tracking unit 173 tracks the initial contour position set at the tracking start temporal phase "t1=E0" by the setting unit 172, in the pieces of ultrasound image data "I(t2) to I(tn)" respectively corresponding to the remaining temporal phases ["t2" to "tn=E1"] other than the tracking start temporal phase "t1=E0".

According to a conventional technique, the position of an initial region of interest (an initial contour position) is tracked by performing a speckle tracking process. In other words, according to the conventional technique, the positions of the region of interest in the pieces of ultrasound image data corresponding to the remaining temporal phases "t2 to tn=E1" are obtained by automatically tracking the initial contour position while using movement information (motion vectors) obtained by performing a local pattern matching process or implementing an optical flow method. According to the conventional technique, however, the extent of pattern change is large, among the frames or among the volumes in an early diastolic phase or a systolic peak phase where the strain rate of the heart is large.

For this reason, when using the speckle tracking process, it is difficult to accurately estimate the motion vectors if the frame rate or the volume rate is insufficient. In particular, when two-dimensional image data is used, the tracked contour is influenced by a movement of going through a scanned cross-sectional plane (which is called a "through-plane" movement). It is therefore even more difficult to accurately estimate the motion vectors, because the pattern change among the frames is even larger.

Further, if the image quality of the moving image data is low due to noise or artifacts, it is difficult to accurately estimate the motion vectors in such a part where the unnecessary components are mixed in. When it is not possible to accurately estimate the movement information for any of the various factors described above, a tracking failure occurs, and as a result, it is not possible to accurately analyze the wall motion.

To cope with this situation, a method is known by which a tracking point is detected where the movements conflict with each other between a contour position obtained as a tracking result and the initial contour position, so as to correct the position of the detected tracking point. This method, however, is based on a premise that the positions of the tracking points that are in the surroundings of the detected tracking point are accurate. In the temporal phases mentioned above in which the extent of pattern change is large, the estimation of the movement information fails in a large area. Consequently, the premise is not fulfilled in the early diastolic phase and the systolic peak phase, and it is therefore not possible to perform the tracking process with a high level of precision.

Further, another method is also known by which the user specifies a region of an image where noise components are mixed in, so as to provide a contour position in the region specified by the user, based on the position information of the contour tracked in a region other than the specified region. This method, however, requires the user to manually correct the contour in the tracking-failure position and thus demands labor.

Yet another method is also known by which a final three-dimensional contour is determined by calculating a linear sum of a three-dimensional contour shape based on the image data and a three-dimensional contour shape based on an optical flow. Although this method is applicable to a contour tracking process using three-dimensional moving image data, the capability of this method is restricted when applied to a contour tracking process using two-dimensional moving image data, because it is not possible to eliminate the influence of the "through-plane" movements described above. Further, at this time, no method that clearly indicates the conditions under which the linear sum should be calculated is known.

To cope with these situations, the tracking unit 173 illustrated in FIG. 1 performs a tracking process described below for the purpose of accurately obtaining a tracking result of the region of interest. Specifically, the tracking unit 173 illustrated in FIG. 1 obtains first position information of a region estimated as the region of interest based on movement information, with respect to the pieces of ultrasound image data corresponding to the remaining temporal phases. Further, the tracking unit 173 illustrated in FIG. 1 obtains second position information of a region estimated as the region of interest based on information (e.g., shape information) other than the movement information, with respect to the pieces of ultrasound image data corresponding to the remaining temporal phases. In other words, the tracking unit 173 functions as an estimating unit that obtains the first position information and the second position information. Further, the tracking unit 173 illustrated in FIG. 1 obtains position information resulting from combining the first position information with the second position information based on a reliability index related to reliability of the movement information, as position information of the region of interest. As a result, the tracking unit 173 illustrated in FIG. 1 tracks the region of interest in the pieces of ultrasound image data corresponding to the remaining temporal phases. In this situation, the "reliability index" may be defined as "movement quality", which is the quality of the movement information. In the following sections, the "reliability index" may be referred to as "movement quality".

Figure 4:
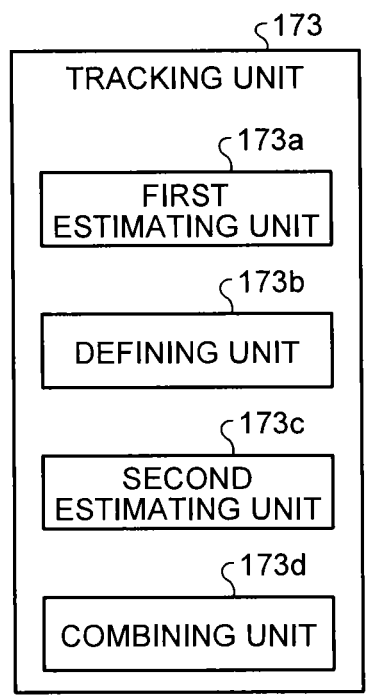
FIG. 4 is a block diagram of an exemplary configuration of a tracking unit illustrated in FIG. 1.

FIG. 4 is a block diagram of an exemplary configuration of the tracking unit illustrated in FIG. 1. To perform the tracking process described above, the tracking unit 173 includes, as illustrated in FIG. 4 for example, a first estimating unit 173a, a defining unit 173b, a second estimating unit 173c, and a combining unit 173d. The first estimating unit 173a and the second estimating unit 173c described below may be installed as an estimating unit in the image processing unit 17, separately from the tracking unit 173.

The first estimating unit 173a performs a tracking process on the region of interest based on movement information, i.e., a speckle tracking process. In other words, the first estimating unit 173a estimates the movement information between first image data, which is ultrasound image data in a first temporal phase, and second image data, which is ultrasound image data in a second temporal phase that is temporally adjacent to the first temporal phase, and further estimates first position information in the second image data by moving the region of interest in the first image data based on the estimated movement information.

More specifically, the first estimating unit 173a calculates motion vectors at each of a plurality of points in a region that contains the region of interest. More specifically, the first estimating unit 173a calculates the motion vectors at each of the plurality of points, by performing a template matching process. Further, for each of the tracking points structuring the region of interest, the first estimating unit 173a estimates a motion vector at the tracking point, by using a group of remaining motion vectors obtained by eliminating statistically-abnormal motion vectors from a group of motion vectors obtained from a segment having a predetermined size and containing the tracking point. The first estimating unit 173a estimates the first position information by using the motion vectors at the tracking points in this manner. Further, the first estimating unit 173a estimates the first position information by estimating the motion vectors at the tracking points that structure the region of interest, while using the group of remaining motion vectors obtained by eliminating the statistically-abnormal motion vectors from the obtained group of motion vectors.

The defining unit 173b defines the reliability index (the movement quality) based on at least one of variables obtained from processes performed by the first estimating unit 173a. The second estimating unit 173c estimates second position information in the second image data based on information (e.g., shape information) other than the movement information. The combining unit 173d obtains position information resulting from combining the first position information with the second position information based on the reliability index (the movement quality), as position information of the region of interest in the second image data.

Next, examples of the specific processes performed by the functional units described above will be explained in detail, with reference to FIGS. 5A to 16. FIGS. 5A to 16 are drawings for explaining the tracking unit according to the first embodiment. In the following sections, an example will be explained in which the initial contour position "C(t1)" of the left ventricular inner layer illustrated in the bottom section of FIG. 3 is tracked in the pieces of ultrasound image data corresponding to the remaining temporal phases "t2 to tn=E1". By performing the process described below, it is also possible to track the initial contour position "D(t1)" of the myocardial outer layer in a similar manner. Thus, the explanation for the process of tracking the contour position of the myocardial outer layer will be omitted.

Figure 5A:
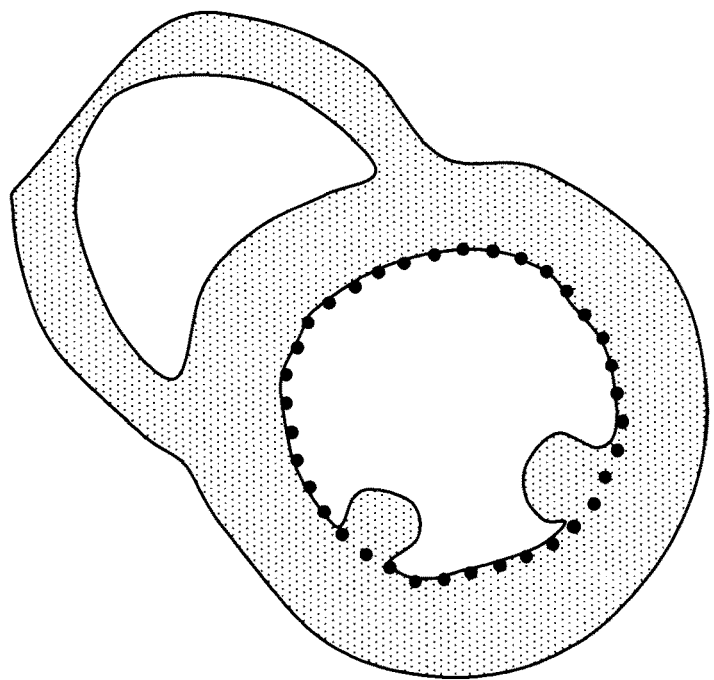
FIG. 5A and FIG. 5B are drawings for explaining the tracking unit according to the first embodiment.
Figure 5B:
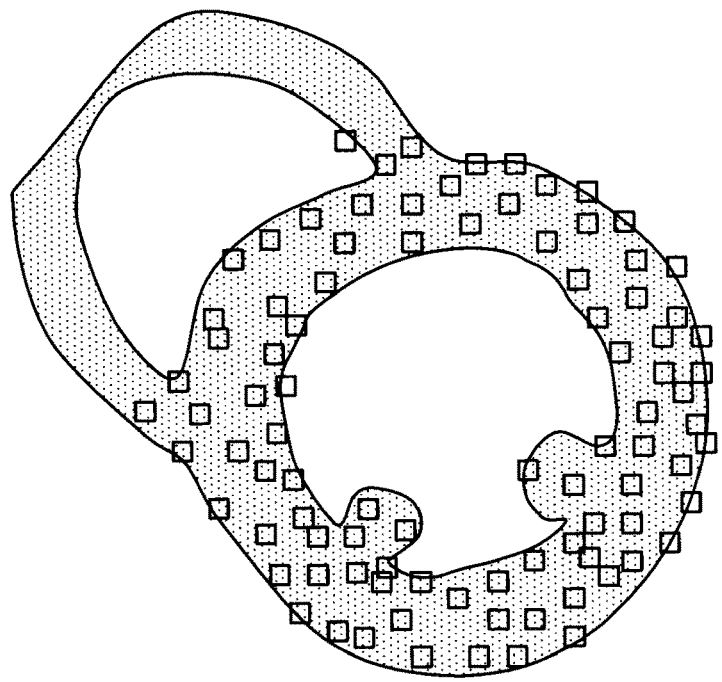

First, as illustrated in FIG. 5A, the first estimating unit 173a sets a plurality of tracking points with the initial contour position "C(t1)". Further, as illustrated in FIG. 5B, the first estimating unit 173a sets a plurality of points in the vicinity of the initial contour position "C(t1)". Each of the plurality of points illustrated in FIG. 5B is a calculation point used for calculating the movement information (the motion vector).

Figure 6:
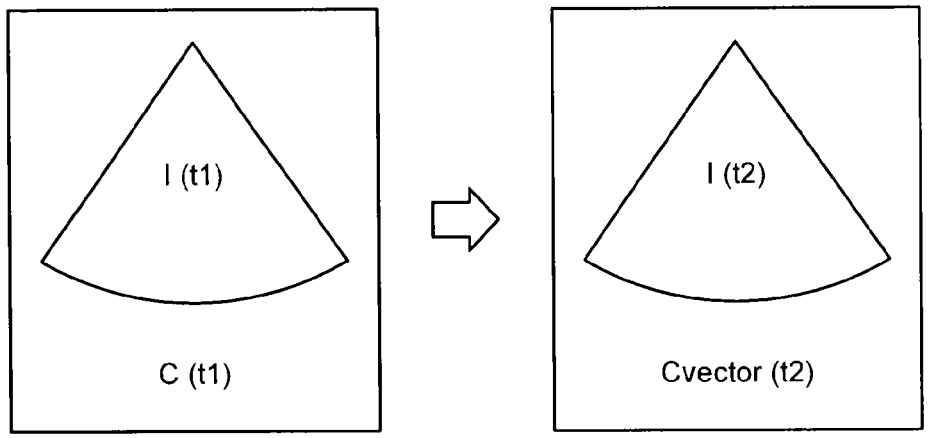

Further, the first estimating unit 173a uses "t1" as the first temporal phase and uses "t2" as the second temporal phase. After that, the first estimating unit 173a estimates movement information between first image data "I(t1)" and second image data "I(t2)" and moves the initial contour position "C(t1)" in I(t1), based on the estimated movement information. As a result, as illustrated in FIG. 6, the first estimating unit 173a estimates first position information "Cvector(t2)" in "I(t2)".

Specifically, the first estimating unit 173a sets template data for each of the plurality of calculation points set in "I(t1)". The template data is made up of a plurality of pixels centered about each calculation point. Further, the first estimating unit 173a tracks a position of the template data, which indicates the position to which the template data moves in the following frame, by searching for a region in which the speckle patterns of the template data best match each other between the two frames (i.e., between "I(t1)" and "I(t2)"). In this manner, the first estimating unit 173a calculates the motion vectors at each of the plurality of calculation points in "I(t1)". In the following sections, a set made up of the motion vectors at the plurality of calculation points in "I(t1)" will be referred to as {Mv0}. In other words, {Mv0} is a group of motion vectors each of which was calculated at a different one of the plurality of calculation points.

Figure 7:
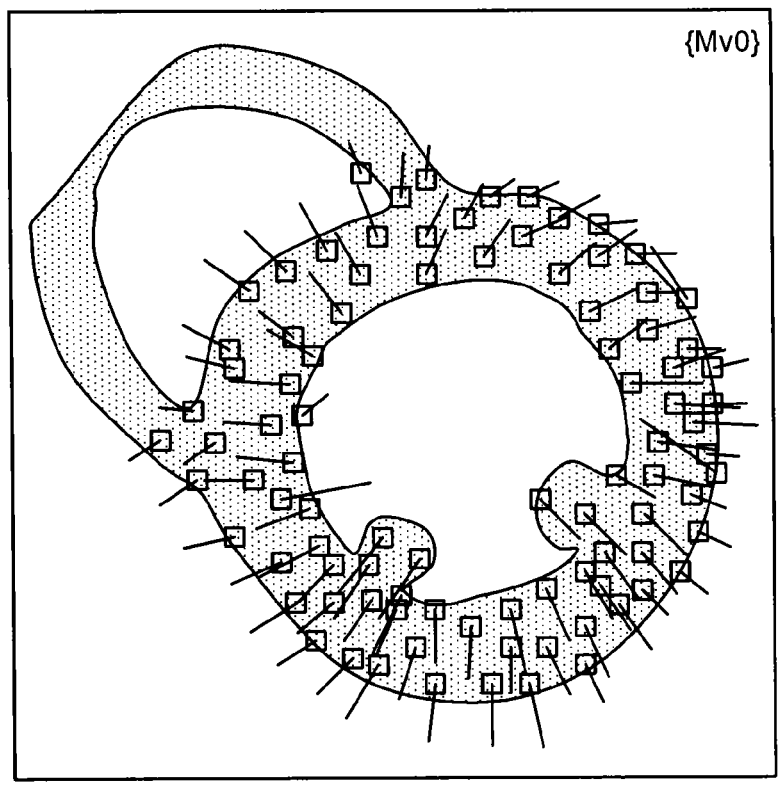

FIG. 7 illustrates an example of the group of motion vectors {Mv0} calculated by the first estimating unit 173a. In FIG. 7, the white squares indicate the calculation points, whereas the line segments extending from the white squares are the motion vectors. The group of motion vectors illustrated in FIG. 7 schematically illustrates a group of motion vectors that are calculated between pieces of image data corresponding to early diastole during which the cardiac chamber expands.

Figure 8:
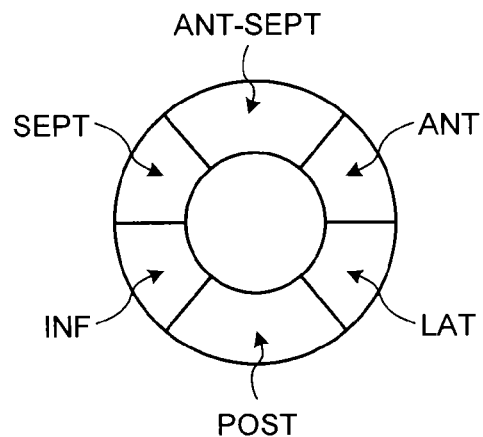

Further, the first estimating unit 173a divides the tracking points illustrated in FIG. 5A into units of segments each having a predetermined size. For example, as illustrated in FIG. 8, the first estimating unit 173*a* divides the left ventricular myocardia on a short-axis cross-sectional plane into six segments such as "anteroseptal (ANT-SEPT), anterior (ANT), lateral (LAT), posterior (POST), inferior (INF), and septal (SEPT)", by using divided regions recommended by the American Society of Echocardiography and the American Heart Association. As a result, each of the tracking points illustrated in FIG. 5A is contained in one of the six segments illustrated in FIG. 8. Also, each of the calculation points illustrated in FIG. 5B is contained in one of the six segments illustrated in FIG. 8.

After that, the first estimating unit 173*a* calculates a statistical value of each of the segments by performing a statistical process on a group of motion vectors contained in each of the segments and further specifies motion vectors, if any, each having an abnormal statistical value, from each of the segments. After that, the first estimating unit 173*a* determines the set made up of the specified motion vectors (i.e., the set made up of the motion vectors each having an abnormal statistical value) to be {Mv'}. Subsequently, the first estimating unit 173*a* determines a set {Mv} of motion vectors that is obtained by eliminating {Mv'} from {Mv0} to be a group of remaining motion vectors.

For example, the first estimating unit 173*a* calculates a variance value "Vari(s)" of the group of motion vectors in each of the segments. When the six segments illustrated in FIG. 8 are expressed as "s1, ..., s6", the first estimating unit 173*a* calculates six variance values such as "Vari(s1), ..., Vari(s6)". After that, for example, from the group of motion vectors contained in the segment "s1", the first estimating unit 173*a* specifies motion vectors each of which exceeds "α×Vari(s1)" as abnormal motion vectors, where "α" is a predetermined coefficient. An example of an appropriate value of "α" is "2". The first estimating unit 173*a* performs this process on each of the segments "s2, s3, s4, s5, and s6" in a similar manner. As a result, as illustrated in FIG. 9, the first estimating unit 173*a* specifies the group of abnormal motion vectors {Mv'} and further obtains the group of remaining motion vectors {Mv} by eliminating {Mv'} from {Mv0}.

Figure 9:
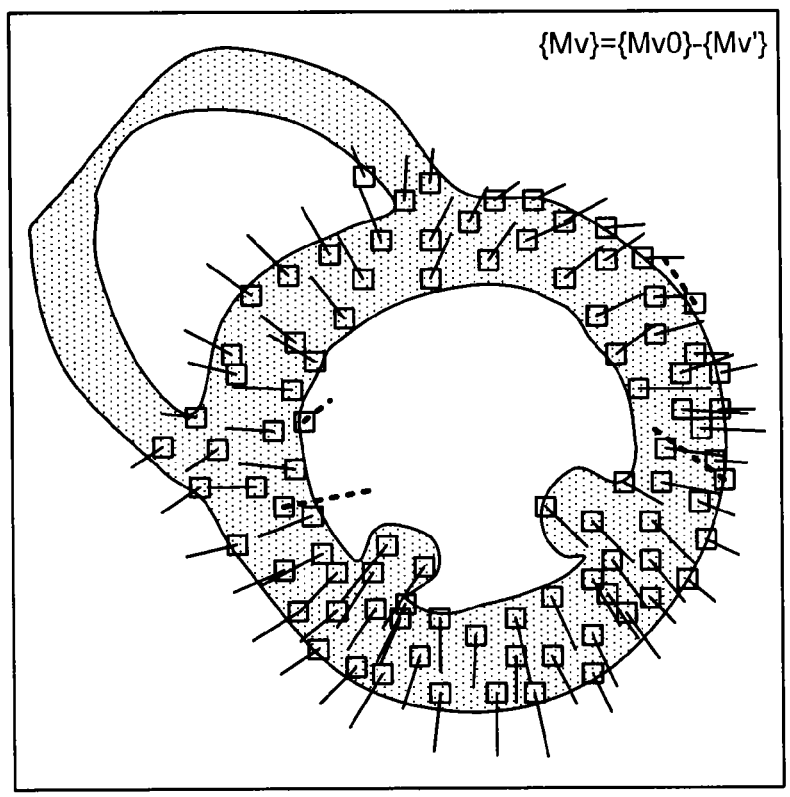

FIG. 9 illustrates an example of the group of abnormal motion vectors specified by the first estimating unit 173*a*. FIG. 9 illustrates four abnormal motion vectors specified by the first estimating unit 173*a* with dotted lines. The group of abnormal motion vectors {Mv'} illustrated in FIG. 9 is a group of abnormal motion vectors identified from the group of motion vectors {Mv0} illustrated in FIG. 7, i.e., the group of motion vectors calculated between the pieces of image data corresponding to early diastole during which the cardiac chamber expands. For this reason, the group of remaining motion vectors {Mv} illustrated in FIG. 9 is made up of motion vectors that are generally oriented outward.

After that, the first estimating unit 173*a* estimates motion vectors at each of the plurality of tracking points that structure the initial contour position "C(t1)", by using the group of remaining motion vectors {Mv}. In the following explanation, any of the motion vectors (i.e., the remaining motion vectors) that are the elements of the set {Mv} will be generalized as "Mv". Further, an arbitrary one of the plurality of tracking points that structure "C(t1)" will be referred to as "p(t1)". The first estimating unit 173*a* obtains a motion vector "Mv_p(t1)" at p(t1), by averaging some motion vectors that are positioned in the vicinity of p(t1) from the group of remaining motion vectors {Mv}.

Figure 10:
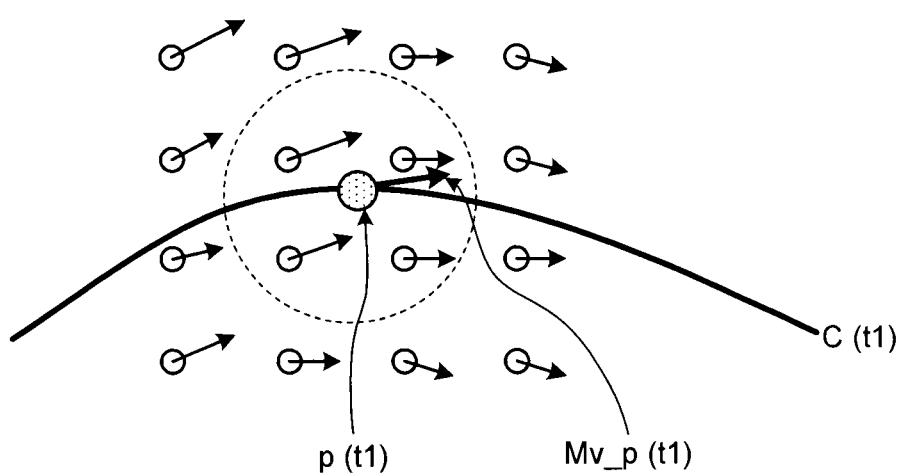

An example of the method described above will be explained with reference to FIG. 10. In FIG. 10, p(t1) is indicated by a circle with dotted hatching. Further, in FIG. 10, the plurality of calculation points positioned in the vicinity of p(t1) are indicated with white circles, whereas the remaining motion vectors at each of the calculation points are indicated with arrows extending from the white circles.

For example, the first estimating unit 173*a* sets a circle that is centered on p(t1) and has a predetermined radius (see the circle drawn with a dotted line in FIG. 10). The length of the predetermined radius may be a value set in advance by a system or may be a value set by the operator. After that, the first estimating unit 173*a* estimates the motion vector "Mv_p(t1)" at p(t1) by averaging the plurality of remaining motion vectors (the four remaining motion vectors in FIG. 10) contained in the circle set for p(t1). The first estimating unit 173*a* performs this process on each of all the tracking points, by using {Mv}.

Figure 11:
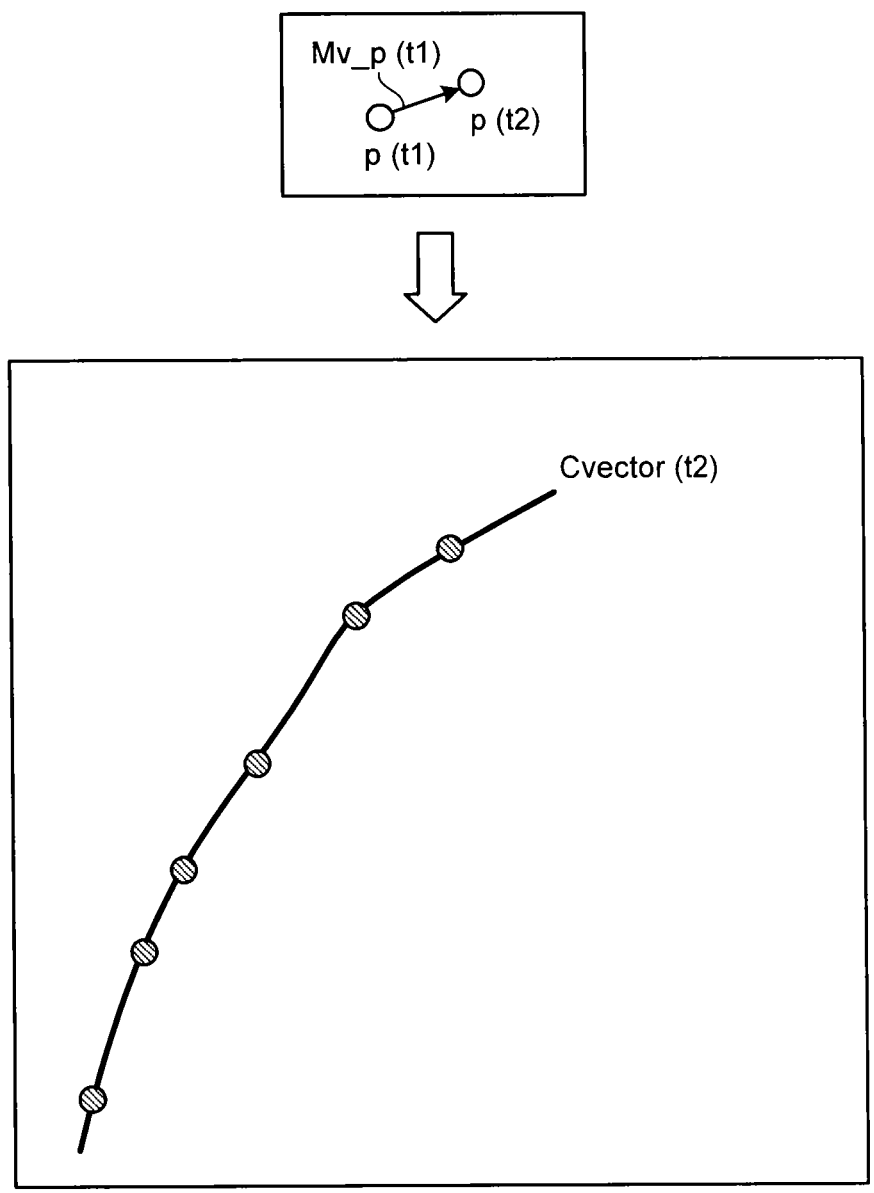

After that, as illustrated in the top section of FIG. 11, the first estimating unit 173*a* estimates, as the first position information, the position of a point p(t2) obtained by moving p(t1) by Mv_p(t1). As a result, as illustrated in the bottom section of FIG. 11, the first estimating unit 173*a* obtains the first position information "Cvector(t2)" in "I(t2)". In the following explanation, an arbitrary one of the plurality of tracking points that structure "Cvector (t2)" will be referred to as p(t2).

After that, the defining unit 173*b* defines a movement quality "Q_p(t2)", which is a reliability index of "p(t2), by using "at least one of the variables obtained from processes performed by the first estimating unit 173*a*".

As described above, the first estimating unit 173*a* estimates the motion vectors by performing the template matching process. In other words, the first estimating unit 173*a* detects the motion vector at each of the calculation points, by searching for a position in which the most similar pattern is existed in the following temporal phase, with respect to a pattern of shades of the image signal values in the template in the current temporal phase. For this reason, the defining unit 173*b* defines a reliability value "R(Mv)" of each of the individual remaining motion vectors "Mv" that structure the group of remaining motion vectors {Mv}, based on variables obtained from the template matching process performed by the first estimating unit 173*a*. The variables used for defining the reliability value include the following three variables.

A first variable that can be used for defining the reliability value is an average signal value of a standard template used in the template matching process. In other words, if the signal values of a template are extremely small, the template is considered to represent the inside of the cardiac chamber or a white noise region, and not a tissue region that is valid in the matching process. Accordingly, if an average value "Tm" of the signals in a template is small, it is appropriate to set "R(Mv)" to a small value.

Consequently, in one example, the defining unit 173*b* defines "R(Mv)" by using Formula (1) shown below. In Formula (1), "Mth" is a lower limit threshold value set for the signal average value in the standard template. The value "Mth" may be, for example, stored in the internal storage unit 16, in advance. Alternatively, the value "Mth" may be set by the operator, for example.

$$R(Mv) = 1 \quad (Tm \geq Mth) \atop R(Mv) = 0 \quad (Tm < Mth) \Biggr\} \quad (1)$$

In other words, the defining unit 173b defines the reliability value to be "1" for such remaining motion vectors that are calculated by using a standard template of which "Tm" is equal to or larger than "Mth". In contrast, the defining unit 173b defines the reliability value to be "0" for such remaining motion vectors that are calculated by using a standard template of which "Tm" is smaller than "Mth".

A second variable that can be used for defining the reliability value is a signal variance value of the standard template used in the template matching process. In other words, if a pattern of shade of the signal values in the standard template is too uniform, the pattern of shades in a searched area in the following temporal phase is also expected to be almost uniform. In that situation, there is a high possibility that a position where the most similar pattern is existed may be detected all over the place of the second image data. As a result, it is not possible to accurately estimate the motion vectors. Accordingly, if a variance value "Tσ" of the signals in a standard template is small, it is appropriate to set "R(Mv)" to a small value.

Consequently, in one example, the defining unit 173b defines "R(Mv)" by using Formula (2) shown below. In Formula (2), "Sth" is a lower limit threshold value set for the signal variance value in the standard template. The value "Sth" may be, for example, stored in the internal storage unit 16, in advance. Alternatively, the value "Sth" may be set by the operator, for example.

$$\left. \begin{array}{l} R(Mv) = 1 \quad (T\sigma \geq Sth) \\ R(Mv) = 0 \quad (T\sigma < Sth) \end{array} \right\} \quad (2)$$

In other words, the defining unit 173b defines the reliability value to be "1" for such remaining motion vectors that are calculated by using a standard template of which "Tσ" is equal to or larger than "Sth". In contrast, the defining unit 173b defines the reliability value to be "0" for such remaining motion vectors that are calculated by using a standard template of which "Tσ" is smaller than "Sth".

A third variable used for defining the reliability value is a level of similarity between the templates used in the template matching process. The first estimating unit 173a searches for a position in which the pattern in the second image data is most similar to the standard template, by comparing the standard template with a search region at the following temporal phase. Accordingly, it is possible to define the level of similarity indicating how similar the region at the position eventually found in the search is, to the one in the standard template. A typical level of similarity can be expressed by using a cross correlation coefficient "Ck". When an input signal is a real number, the value of "Ck" satisfies "0≤Ck≤1". In the first embodiment where the comparison is made between the pieces of image data, because the input signal is a real number, "0≤Ck≤1" is satisfied. If the level of similarity is low, it means that the extent of pattern change is large in the tracking target site in the course of time between the current temporal phase and the following temporal phase. Accordingly, if the level of similarity "Ck" is small, it is appropriate to set "R(Mv)" to a small value.

Consequently, in one example, the defining unit 173b defines "R(Mv)" by using Formula (3) shown below. In Formula (3), "Cth" is a lower limit threshold value set for the level of similarity in the template matching process. The value "Cth" may be, for example, stored in the internal storage unit 16, in advance. Alternatively, the value "Cth" may be set by the operator, for example.

$$\left. \begin{array}{l} R(Mv) = Ck \quad (Ck \geq Cth) \\ R(Mv) = 0 \quad (Ck < Cth) \end{array} \right\} \quad (3)$$

In other words, the defining unit 173b defines the reliability value to be "Ck" for such remaining motion vectors of which "Ck" is equal to or larger than "Cth". In contrast, the defining unit 173b defines the reliability value to be "0" for such remaining motion vectors of which "Ck" is smaller than "Cth".

In Formula (1) and (2) above, the value of "R(Mv)" is simply determined to be "1" or "0", based on the threshold value. However, it is also acceptable to configure the first embodiment so that "R(Mv)" is defined as a continuous monotone increasing function that uses the control variables presented above. Alternatively, the value of "R(Mv)" may be defined by using a combination of at least one of the three control variables presented above. In the first embodiment, it is desirable to determine a final value of "R(Mv)" by using all of the three control variables presented above. In that situation, the value of "R(Mv)" is defined by a function that uses all three of "Tm, Tσ, and Ck" as the control variables thereof.

By defining the value "R(Mv)" of each of the individual remaining motion vectors in the manner described above, the defining unit 173b evaluates the quality (the reliability) of the individual remaining motion vectors. Further, as explained below, the defining unit 173b evaluates the quality (the reliability) of the motion vectors in a region (a segment) having a predetermined size, by using a spatial continuity of a plurality of motion vectors.

In movements of biological tissues, a extreme spatial discontinuity is unlikely to occur. On the other hand, in a speckle tracking process, there is a possibility that inappropriate motion vectors may be detected due to an influence of speckle noises. For this reason, as explained above, the first estimating unit 173a obtains the group of remaining motion vectors {Mv}, by calculating the variance value "Vari(s)" of the group of motion vectors in each of the segments and eliminating the group of motion vectors {Mv'} having abnormal values exceeding the predetermined threshold value as the group of abnormal mobile vectors, from {Mv0}.

Accordingly, the defining unit 173b uses variables obtained from statistical processes performed by the first estimating unit 173a, as the variables used for defining the movement quality (the reliability index).

A first variable obtained from a statistical process is a variance value of the motion vectors in a vicinal region of each of the plurality of tracking points. In this situation, it is considered that the smaller the value of the spatial variance of the motion vectors in the vicinal region is, the lower the movement quality is. As the vicinal regions, the defining unit 173b uses the six segments "s1, . . . , s6" presented above, for example. In that situation, the defining unit 173b obtains the variance value "Vari(s)" of the group of motion vectors in each of the segments, from the first estimating unit 173a. In other words, the defining unit 173b obtains "Vari(s1), . . . , Vari(s6)" corresponding to the six segments "s1, . . . , s6", respectively.

A second variable obtained from a statistical process is the density of the motion vectors determined to be in the group of remaining motion vectors in the vicinal region of each of the plurality of tracking points. In this situation, it is considered that the smaller the density value of the valid motion vectors (the remaining motion vectors) in the vicinal region is, the lower the movement quality is. As the vicinal regions, the defining unit 173b uses the six segments "s1, . . . , s6" presented above, for example. In that situation, for example, the defining unit 173b calculates a density value "ρ(s)" of the valid motion vectors in each of the segments "s", by obtaining the quantity of members of {Mv0} in the segment "s" and the quantity of members of {Mv} in the segment "s" from the first estimating unit 173a. In one example, the defining unit 173b defines "ρ(s)" by using Formula (4) shown below.

$$\rho(s)=\text{"quantity of members of } \{MV\} \text{ in } s\text{"}/\text{"quantity of members of } \{Mv0\} \text{ in } s\text{"} \quad (4)$$

In other words, the defining unit 173b defines the value obtained by dividing the quantity of members of {Mv0} in the segment "s" by the quantity of members of {Mv} in the segment "s", as "ρ(s)". By using Formula (4), the defining unit 173b obtains "ρ(s1), . . . , ρ(s6)" corresponding to the six segments "s1, . . . , s6", respectively.

After that, by using at least one selected from "R(Mv)", "ρ(s)", and "Vari(s)" described above, the defining unit 173b calculates a movement quality "Q(s,Mv)" of the motion vectors at each of the calculation points calculated by the first estimating unit 173a. For example, the defining unit 173b defines "Q(s,Mv)" by using Formula (5) shown below. In Formula (5), "Lth" is a lower limit threshold value set for the spatial variance value of the motion vector. The value "Lth" may be, for example, stored in the internal storage unit 16, in advance. Alternatively, the value "Lth" may be set by the operator, for example.

$$\left. \begin{array}{ll} Q(s, Mv) = R(Mv) * \rho(s) & (Lth \geq Vari(s)) \\ Q(s, Mv) = 0 & (Lth < Vari(s)) \end{array} \right\} \quad (5)$$

In other words, the defining unit 173b sets the movement quality to "0" for the motion vectors that are positioned at a calculation point contained in any of the segments of which "Vari(s)" is smaller than "Lth". For example, if "Vari(s2)" is smaller than "Lth", the defining unit 173b sets a movement quality to "0" for the motion vectors at the calculation points contained in "s2".

Further, for each of the motion vectors at the calculation points contained in any of the segments of which "Vari(s)" is equal to or larger than "Lth", the defining unit 173b calculates a movement quality for the individual motion vectors. For example, if "Vari(s5)" is equal to or larger than "Lth", the defining unit 173b calculates "Q(s5,Mv)" by multiplying the reliability value "R(Mv)" of the motion vector "Mv" at each of the calculation points contained in "s5" by "ρ(s5)".

The defining unit 173b thus defines the movement quality (the reliability index) of each of the remaining motion vectors used for estimating "Cvector(t2)". In another example, the defining unit 173b may define the movement quality of each of the remaining motion vectors by using "R(Mv)". In yet another example, the defining unit 173b may define the movement quality of each of the remaining motion vectors by using at least one of "Vari(s)" and "ρ(s)".

Figure 12:
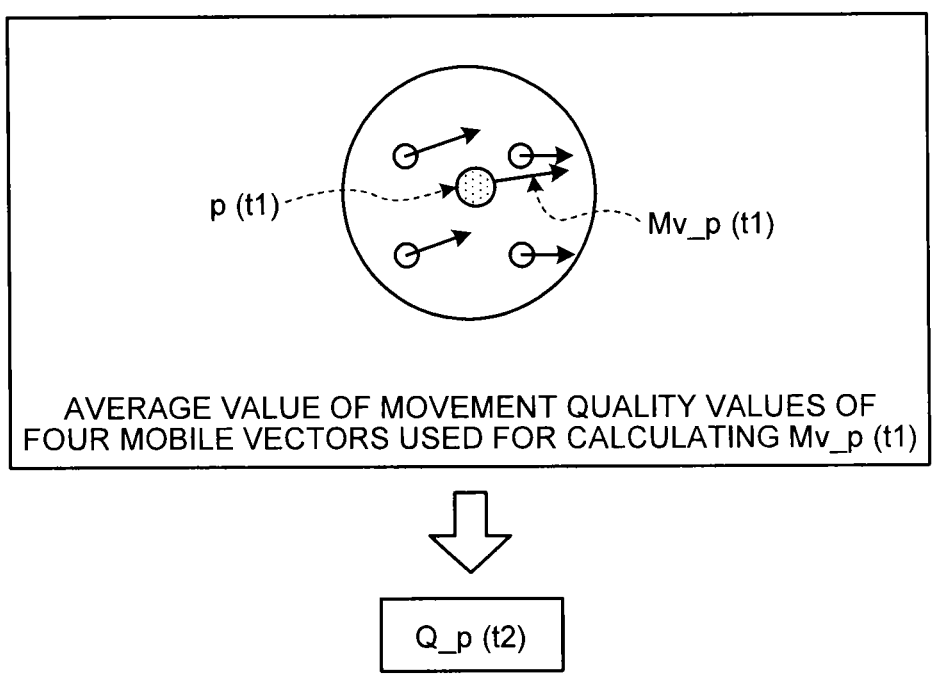

Further, the defining unit 173b defines the movement quality "Q_p(t2)", which is a reliability index of "p(t2) that has moved from p(t1)", by averaging the movement quality some remaining motion vectors that are positioned in the vicinity of p(t1). For example, as illustrated in FIG. 12, the defining unit 173b calculates an average value of the movement quality of four motion vectors (remaining motion vectors) used for calculating "Mv_p(t1)", as "Q_p(t2)".

It is desirable that the process performed by the first estimating unit 173a is performed in parallel with the process performed by the defining unit 173b, so as to be in synchronization with each other for each of the temporal phases served as the tracking targets. This parallel process may be realized under the control of the controlling unit 18. Further, the number and the size of the segments used in the processes described above may be changed by the operator to an arbitrary number and to an arbitrary size, for example. Further, the segments used in the process performed by the first estimating unit 173a may be different from the segments used in the process performed by the defining unit 173b.

Subsequently, the second estimating unit 173c estimates the second position information by using at least one of the following pieces of position information: position information obtained from a first process; position information obtained from a second process; and position information obtained from a third process described below.

Figure 13A:
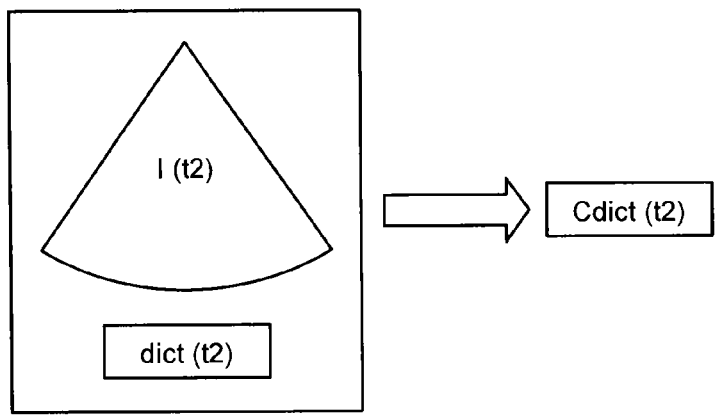

In the first process, the second estimating unit 173c estimates position information "Cdict(t)" of the region of interest in the second image data, by comparing the second image data in a temporal phase "t" with shape dictionary information "dict(t)" in the same temporal phase. When performing the first process, the internal storage unit 16 has stored therein, in advance, shape dictionaries of the left ventricular myocardium corresponding to all the cardiac phases, for example. Further, because the second image data is "I(t2)", the second estimating unit 173c obtains a shape dictionary "dict(t2)" in the cardiac phase corresponding to the temporal phase "t2", from the internal storage unit 16. After that, as illustrated in FIG. 13A, the second estimating unit 173c estimates position information "Cdict(t2)" of the region of interest (the contour) in "I(t2)", by comparing "I(t2)" with "dict(t2)" while using a function of a discriminator. As the discriminator, an algorithm that uses random forest both when learning the shape dictionaries and when discriminating data is known as a fast method. Thus, these methods are considered to be a desirable example in the first embodiment.

In the second process, the second estimating unit 173c estimates position information "Ceng(t)" of the region of interest in the second image data corresponding to a temporal phase "t" based on the principle of minimum shape energy. In one example, the second estimating unit 173c uses a "snake" method, which is known as a type of Active Contour Model (ACM). The second estimating unit 173c sets a contour line in the vicinity of the boundary of the cardiac chamber within the second image data served as a processing target. For example, the contour line may be set based on C(t1) or may be set based on brightness level information.

Figure 13B:
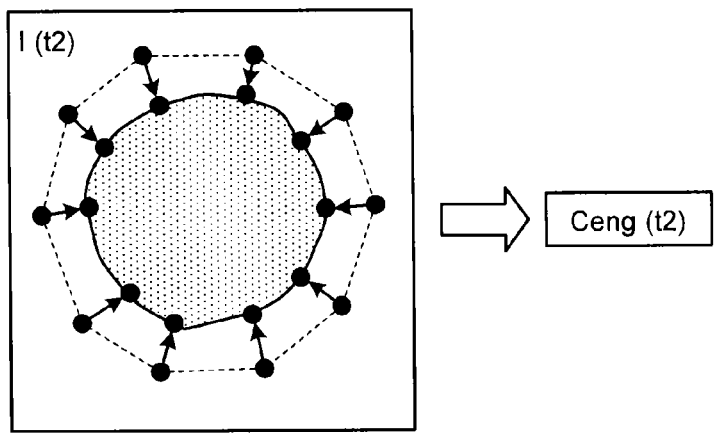

Further, the second estimating unit 173c repeatedly corrects the position and the shape of the contour line until the value of an evaluation function of the shape energy is at the minimum. For example, the second estimating unit 173c repeatedly corrects the position and the shape of the contour line until the contour line is positioned in a part where the brightness level drastically changes, the brightness level values inside the contour line become uniform, and the contour line becomes short and has a smooth shape. As a result, as illustrated in FIG. 13B, the second estimating unit 173c estimates the position information "Ceng(t2)" of the region of interest (the contour) in the second image data "I(t2)".

In the third process, the second estimating unit 173c estimates position information "Cfit(t)" of the region of interest in the second image data corresponding to a temporal phase "t", by performing a process that includes a fitting process based on the least squares method. In this situation, to obtain position information having high reliability by the fitting process based on the least squares method, a plurality of control points "r(t)" that contain position information having a certain level of accuracy are required, as inputs of the fitting process. For this reason, the second estimating unit 173c performs the third process only on a site where the movement quality (the reliability index) is degraded.

As explained above, the movement quality "Q_p(t2)" is defined for each of the tracking points p(t2) structuring "Cvector(t2)" in the second image data "I(t2)". For this reason, the second estimating unit 173c specifies such points p(t2) of which the movement quality value "Q_p(t2)" is equal to or smaller than a predetermined value. For example, as illustrated in the left section of FIG. 13C, the second estimating unit 173c specifies the points p(t2) contained in the dotted circle. After that, the second estimating unit 173c determines a set made up of points p(t2) other than the points p(t2) contained in the dotted circle as a group of control points "r(t2)" used for performing the fitting process and further performs the least squares fitting process by using the determined group of control points "r(t2)". As a result, as illustrated in the right section of FIG. 13C, for example, the second estimating unit 173c estimates the position information "Cfit(t2)" of the region of interest (the contour) in the second image data "I(t2)".

In the third process, when the movement quality of Cvector(t) is degraded by an influence of local noise, "Cfit(t)" is obtained by appropriately interpolating only a part of the contour position that is positioned at a site where the movement quality is degraded, by using the position of Cvector(t) in the surroundings where the movement quality is higher. In other words, the third process is a process to estimate the contour shape of the site where the movement quality (the reliability index) is degraded based on the contour shape in the surroundings where the movement quality (the reliability index) is higher. Alternatively, the second estimating unit 173c may obtain "Cdict(t)" by performing the first process or may obtain "Ceng(t)" by performing the second process, only in a local position of Cvector(t) where the movement quality is degraded.

After that, the second estimating unit 173c defines second position information "Cmodel(t)" in the second image data by using at least one selected from "Cdict(t)", "Ceng(t)", and "Cfit(t)". Because the second image data is expressed as "I(t2)", the second estimating unit 173c defines the second position information "Cmodel(t2)" in "I(t2)" by using at least one selected from "Cdict(t2)", "Ceng(t2)", and "Cfit(t2)".

When performing only the first process, the second estimating unit 173c determines "Cdict(t2)" to be "Cmodel(t2)". When performing only the second process, the second estimating unit 173c determines "Ceng(t2)" to be "Cmodel(t2)". Further, when performing only the third process, the second estimating unit 173c determines "Cfit(t2)" to be "Cmodel(t2)".

In these situations, if "Cvector(t)" and "Q_p(t)" have been obtained, the second estimating unit 173c is able to estimate "Cfit(t)". On the contrary, even if "Cvector(t)" and "Q_p(t)" have not been obtained, the second estimating unit 173c is able to estimate "Cdict(t)" and to estimate "Ceng(t)". Further, the second estimating unit 173c is able to perform the estimation of "Cdict(t)" and the estimation of "Ceng(t)" independently of each other.

In other words, the second estimating unit 173c is able to estimate these three pieces of position information. For this reason, the second estimating unit 173c may provide "Cmodel(t)" by performing a linear addition on all of the three pieces of position information or on two pieces of position information selected out of the three. For example, the second estimating unit 173c calculates "Cmodel(t)" by averaging a plurality of contour positions.

It should be noted, however, that it is necessary to prepare the shape dictionaries for all the temporal phases in order to obtain "Cdict(t)". Because hearts have a variety of shapes, it is necessary to have, generally speaking, hundreds or more data even for one temporal phase, in order to construct the shape dictionaries with a high level of precision. It is therefore not practical to use the shape dictionaries of all the temporal phases corresponding to the cardiac cycle.

For this reason, for a specific temporal phase for which shape dictionary information is available, the second estimating unit 173c determines the position information obtained from the first process to be the second position information. In one example, for a specific temporal phase in which the shape of the tissue (the myocardium) exhibits a large local strain, the second estimating unit 173c determines the position information obtained from the first process to be the second position information. Further, in the temporal phases other than the specific temporal phase described above, it is desirable that the second estimating unit 173c determines the position information obtained from the second process or the position information resulting from combining the position information obtained from the second process with the position information obtained from the third process, to be the second position information.

In this situation, the specific temporal phase may be a large early diastolic (e') phase or a systolic peak (s') phase each of which is a typical temporal phase where the strain rate of the heart is expected to be large and where a tracking failure is likely to occur. When changing the second position information in accordance with a specific phase, the second estimating unit 173c determines "Cdict(t)" to be "Cmodel(t)" in a specific temporal phase (e',s') by the first process. Further, when changing the second position information in accordance with a specific phase, the second estimating unit 173c determines "Ceng(t)" to be "Cmodel(t)" in the temporal phases other than the specific temporal phase. Alternatively, when changing the second position information in accordance with a specific phase, the second estimating unit 173c determines a contour position obtained by performing a linear addition on "Ceng(t)" and "Cfit(t)" to be "Cmodel(t)" in the temporal phases other than the specific temporal phase.

In this situation, the second estimating unit 173c is able to perform the first process and the second process in parallel with the processes performed by the first estimating unit 173a and the defining unit 173b. Alternatively, the second estimating unit 173c is able to perform the first process and the second process, independently of the processes performed by the first estimating unit 173a and the defining unit 173b. In other words, the second estimating unit 173c may perform the first process and the second process for all the remaining temporal phases, at the time point when the obtaining unit 171 has obtained the moving image data. Further, if the third process is performed, it is desirable that the second estimating unit 173c performs the third process in parallel with the processes performed by the first estimating unit 173a and the defining unit 173b, so as to be synchronized for each of the temporal phases served as the tracking targets. The progress of the processes performed by the units can be controlled by the controlling unit 18.

As a result of the processes described above, the first estimating unit 173a obtains, as illustrated in the top section of FIG. 14, the contour position "Cvector(t2)" based on the contour position "C(t1)" and the movement information {Mv}, as the set made up of the plurality of tracking points "p(t2)". In contrast, the second estimating unit 173c obtains, as illustrated in the top section of FIG. 14, the contour position "Cmodel(t2)" based on the information (e.g., the shape information) other than the movement information, as the set made up of the contour control points "q(t2)" of which the positions and the number of pieces are independent of those of "p(t2)". In this situation, "Cvector(t2)" is the first position information, whereas "Cmodel(t2)" is the second position information. Further, the movement quality (the reliability index) is defined for each of the plurality of tracking points "p(t2)".

After that, the combining unit 173d combines the first position information with the second position information based on the reliability index (the movement quality). Specifically, the combining unit 173d performs a weighted addition on the first position information and the second position information based on the reliability index (the movement quality). More specifically, the combining unit 173d performs the weighted addition on the first position information and the second position information in such a manner that a larger weight is applied to the first position information if the reliability index (the movement quality) is higher. To perform this process, the combining unit 173d obtains a plurality of points "cross_p(t2)" on "Cmodel(t2)" that respectively correspond to the plurality of tracking points "p(t2)". For example, as illustrated in the top section of FIG. 14, the combining unit 173d calculates a normal vector "Vnormal_p(t2)" at each of the points "p(t2)" on the contour line defined as "Cvector(t2)". After that, as illustrated in the top section of FIG. 14, the combining unit 173d determines the intersection points of the normal vectors "Vnormal_p(t2)" and the contour line defined as "Cmodel (t2)" to be "cross_p(t2)".

Subsequently, as illustrated in the bottom section of FIG. 14, the combining unit 173d converts "Cmodel(t2)" into "Cmodel(t2)'" structured with the plurality of points "cross_p(t2)".

As a result, the combining unit 173d obtains the plurality of points "cross_p(t2)" on Cmodel(t2) that respectively correspond to the plurality of tracking points "p(t2)". The movement quality value "Q_p(t2)" at the points "p(t2)" is now a movement quality value "Q_cross_p(t2)" at the points "cross_p(t2)".

In this situation, to make generalization, the first position information at a temporal phase "t" is referred to as "Cvector (t)" structured with the plurality of tracking points "p(t)", whereas the movement quality value at each of the tracking points "p(t)" is referred to as "Q_p(t)". Further, to make generalization, the second position information in a temporal phase "t" is referred to as "Cmodel(t)" structured with the plurality of control points "q(t)", whereas the converted second position information obtained by converting "Cmodel(t)" with the plurality of points "cross_p(t2)" is referred to as "Cmodel(t)'". In that situation, for example, the combining unit 173d calculates a contour position "C(t)" at the temporal phase "t", by performing a weighted addition on "Cvector(t)" and "Cmodel(t)'" based on "Q_p(t)", by using Formula (6) shown below. In this situation, "Q_p(t)" is normalized so as to satisfy "0≤Q_p(t)≤1" according to the definition described above.

$$C(t) = Q\_p(t) * Cvector(t) + (1 - Q\_p(t)) * Cmodel(t)' \quad (6)$$
$$(0 \le Q\_p(t) \le 1)$$

In other words, in the first term of Formula (6), a position vector is calculated by multiplying the position vector at the tracking point "p(t2)" on "Cvector(t2)" by the weight "Q_p (t2)". In the second term of Formula (6), a position vector is calculated by multiplying the position vector at the point "cross_p(t2)" on "Cmodel(t2)'" by a weight "1−Q_p(t2)". Consequently, by using Formula (6), the point defined by a position vector obtained by adding the two position vectors together is estimated as a point that structures the contour position "C(t2)" in "I(t2)" at the temporal phase "t2". By using this method, if the movement quality is sufficiently high (i.e., Q_p(t)=1) for each of the tracking points p(t), the final contour position C(t) is determined by Cvector(t) based on the movement information, like in the conventional example. In contrast, for such a position or such a temporal phase in which the movement quality is extremely low (i.e., Q_p(t)=0), C(t) is determined by Cmodel(t)' based on the information other than the movement information. Further, if the movement quality is moderate (i.e., 0<Q_p(t)<1), both of the contour positions are combined in accordance with the value of Q_p(t), so that a probable contour position is automatically provided in accordance with the movement quality. Further, because the number of tracking points p(t) structuring C(t) is constant, the tracking operation is completed when the contour position is determined.

Figure 15:
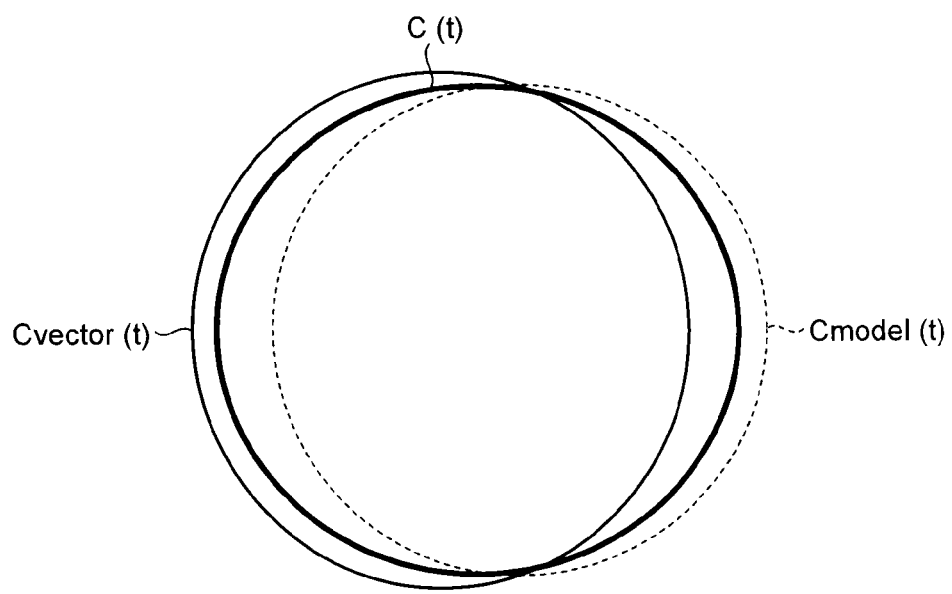

FIG. 15 is a schematic drawing that schematically illustrates, with respect to a short-axis view, the contour position "C(t)" obtained as a result of the combining unit 173d combining "Cvector(t)" with "Cmodel(t)", based on "Q_p (t)". FIG. 15 illustrates an example in which the movement quality is high for the wall on the left-hand side, whereas the movement quality is low for the wall on the right-hand side. In other words, in the example illustrated in FIG. 15, the position of C(t) is reconstructed so as to be positioned close to "Cvector(t)" on the left-hand side and so as to be positioned close to "Cmodel(t)" on the right-hand side.

Figure 16:
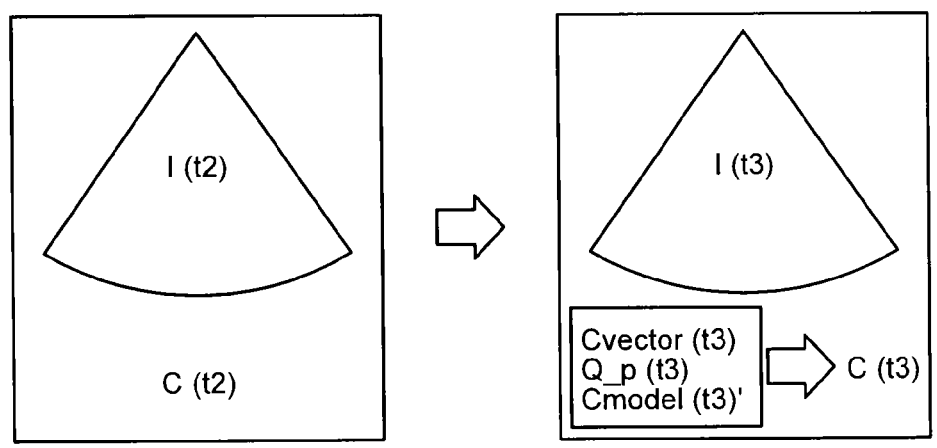

Further, the combining unit 173d informs the first estimating unit 173a of the plurality of points structuring the contour position "C(t2)" estimated from Formula (6), as the plurality of tracking points "p(t2)". Accordingly, the constituent units of the tracking unit 173 perform the processes explained above after replacing "t1" with "t2" and replace "t2" with "t3". Specifically, as illustrated in FIG. 16, the first estimating unit 173a estimates Cvector(t3) by performing a speckle tracking process between the first image data "I(t2)" and the second image data "I(t3)". The defining unit 173b defines a movement quality "Q_p(t3)" at "p(t3)". Further, the second estimating unit 173c estimates "Cmodel(t3)" in "I(t3)". After that, as illustrated in FIG. 16, the combining unit 173d converts "Cmodel(t3)" into "Cmodel(t3)'" and further estimates a contour position "C(t3)" by combining "Cvector(t3)" with "Cmodel(t3)" based on "Q_p(t3)".

With regard to the contour position of the inner layer, the tracking unit 173 repeatedly performs the processes described above up to the temporal phase "tn=E1". As a result, the tracking unit 173 obtains contour positions "C(t1), C(t2), . . . , C(tn)" of the inner layer corresponding to all the temporal phases. Further, with regard to the contour position of the outer layer, the tracking unit 173 repeatedly performs the processes described above up to the temporal phase "tn=E1". As a result, the tracking unit 173 obtains contour positions "D(t1), D(t2), . . . , D(tn)" of the outer layer corresponding to all the temporal phases.

Further, the motion information calculating unit 174 illustrated in FIG. 1 calculates the motion information of the tissue, by using the position information of the region of interest in each of the pieces of moving image data. For example, the motion information calculating unit 174 calculates various types of physical quantities, such as a strain value and time dependence of a strain rate, as wall motion information. When analyzing cardiac functions, the operator is able to arbitrarily select local wall motion information or overall wall motion information which he/she wishes to use in the evaluation and to cause the motion information calculating unit 174 to calculate the selected type of wall motion information. After that, the controlling unit 18 causes the monitor 2 to display the motion information.

Figure 17:
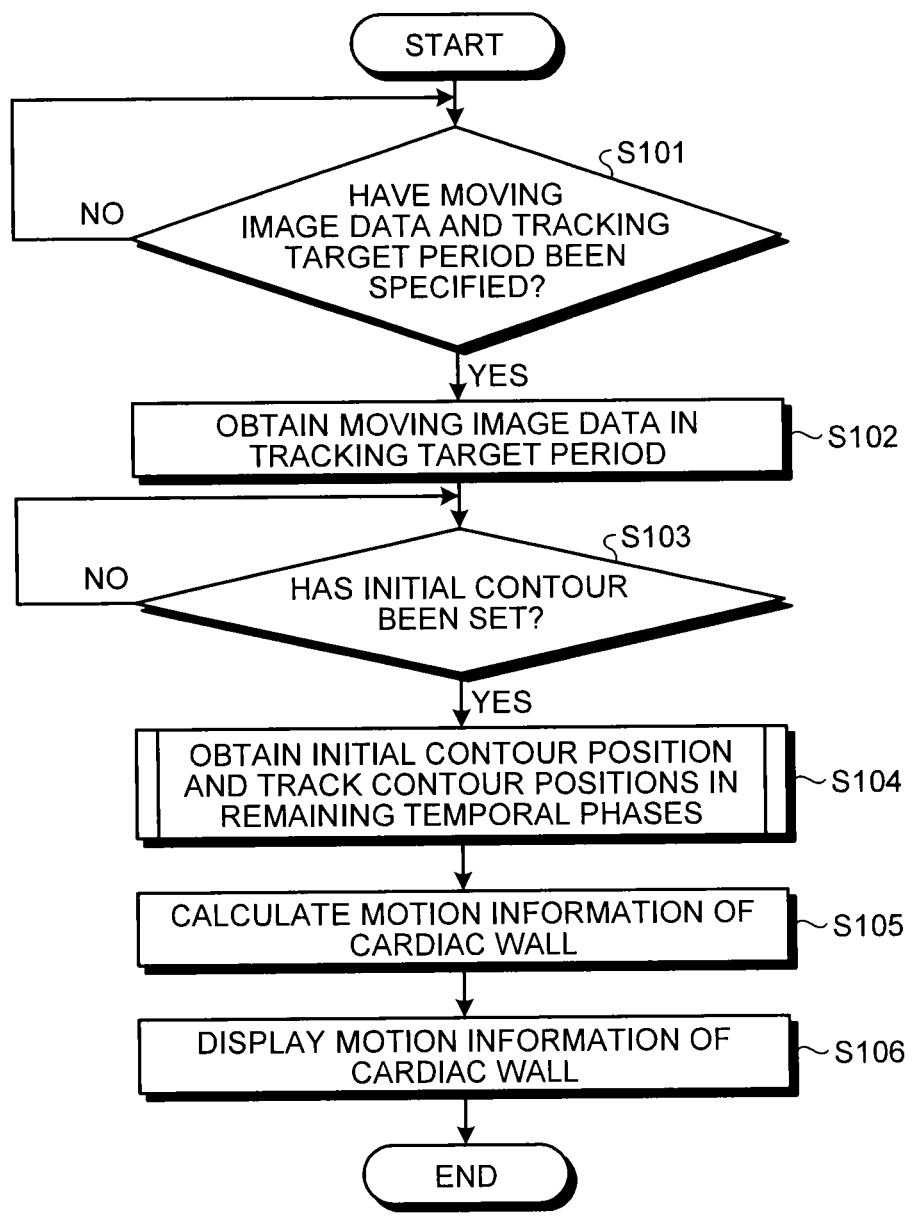
FIG. 17 is a flowchart for explaining an outline of processes performed by the ultrasound diagnostic apparatus according to the first embodiment.
Figure 18:
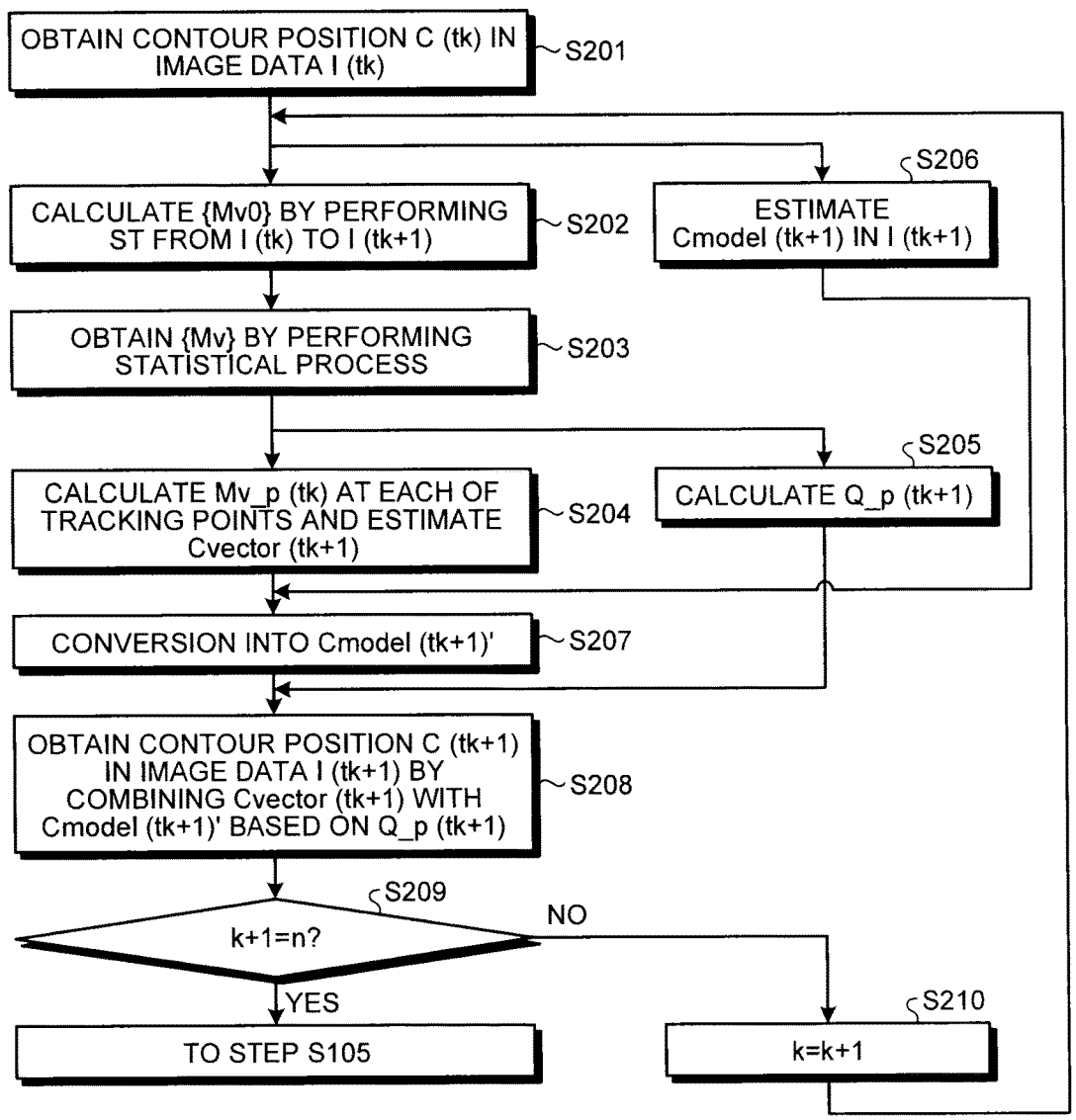
FIG. 18 is a flowchart for explaining exemplary processes performed by the tracking unit according to the first embodiment.

Next, processes performed by the ultrasound diagnostic apparatus according to the first embodiment will be explained, with reference to FIGS. 17 and 18. FIG. 17 is a flowchart for explaining an outline of the processes performed by the ultrasound diagnostic apparatus according to the first embodiment. FIG. 18 is a flowchart for explaining exemplary processes performed by the tracking unit according to the first embodiment.

As illustrated in FIG. 17, the obtaining unit 171 included in the ultrasound diagnostic apparatus according to the first embodiment judges whether a moving image data and a tracking target period have been specified (step S101). If a moving image data and a tracking target period have not been specified (step S101: No), the obtaining unit 171 waits until a moving image data and a tracking target period have been specified.

On the contrary, if a moving image data and a tracking target period have been specified (step S101: Yes), the obtaining unit 171 obtains moving image data in the tracking target period (step S102). After that, the setting unit 172 judges whether the operator has set an initial contour position (step S103). If the operator has not set an initial contour position (step S103: No), the setting unit 172 waits until the operator sets an initial contour position.

On the contrary, if the operator has set an initial contour position (step S103: Yes), the tracking unit 173 obtains the initial contour position and tracks the contour positions in the remaining temporal phases (step S104). After that, when the contour tracking process in the remaining temporal phases has finished, the motion information calculating unit 174 calculates motion information of the cardiac wall (step S105). Under the control of the controlling unit 18, the monitor 2 displays the motion information of the cardiac wall (step S106), and the process is ended.

In this situation, the process at step S104 in FIG. 17 may be realized as a process in the flowchart in FIG. 18. Specifically, the first estimating unit 173a obtains a contour position C(tk) in the image data I(tk) (step S201). In the step S201 for the first time, "tk=t1" is satisfied.

After that, the first estimating unit 173a calculates {Mv0} by performing a speckle tracking (ST) process from I(tk) to I(tk+1) (step S202). Subsequently, the first estimating unit 173a obtains a group of remaining motion vectors {Mv} by performing a statistical process (step S203). The first estimating unit 173a then calculates Mv_p(tk) at each of the tracking points by using {Mv} and estimates Cvector(tk+1) (step S204).

Further, while the process at step S204 is being performed, the defining unit 173b calculates a movement quality Q_p(tk+1), which is a reliability index at each of the tracking points p(tk+1) structuring Cvector(tk+1) (step S205). While the processes at steps S202 to S204 and S205 are being performed, the second estimating unit 173c estimates Cmodel(tk+1) in I(tk+1) (step S206).

After that, the combining unit 173d converts Cmodel(tk+1) into Cmodel(tk+1)' by using Cvector(tk+1) (step S207). Subsequently, the combining unit 173d obtains a contour position C(tk+1) in I(tk+1) by combining Cvector(tk+1) with Cmodel(tk+1)' based on the movement quality Q_p(tk+1) at each of the tracking points p(tk+1) (step S208).

After that, the combining unit 173d judges whether "k+1=n" is satisfied (step S209). If "k+1<n" is satisfied (step S209: No), the combining unit 173d determines that there are one or more temporal phases for which the contour tracking process has not yet been performed and sets k so as to satisfy "k=k+1" (step S210). Further, by using C(tk+1) as C(tk), the tracking unit 173 repeats the processes at step S202 and thereafter.

On the contrary, if "k+1=n" is satisfied (step S209: Yes), the combining unit 173d informs the motion information calculating unit 174 that the contour tracking process has been finished for all the temporal phases, so that the motion information calculating unit 174 starts the process at step S105.

As explained above, according to the first embodiment, to track the region of interest, the positions of the region of interest are estimated based on the movement information, and also, the positions of the region of interest are estimated based on the information other than the movement information. Further, in the first embodiment, the quality of the movement information (the reliability index) is defined based on the various types of information, so that the estimated positions based on the movement information are combined with the estimated positions based on the information other than the movement information, in accordance with the quality (the reliability index). In other words, during the speckle tracking process according to the first embodiment, the local positions where the movement information is insufficient, the local positions where the reliability of the movement information is low, and the local positions where the spatiotemporal consistency of the movement information is low are identified based on the movement quality (the reliability index), so that, in these positions, the final contour positions are determined by using, in combination, the contour positions calculated based on the information other than the movement information.

As a result, according to the first embodiment, even if the estimation capability of the movement information is degraded by the presence of image noise or an insufficient frame rate, it is possible to automatically obtain the positions of the region of interest without experiencing tracking failures of an extreme level. Accordingly, in the first embodiment, it is possible to accurately obtain the tracking result of the region of interest. Further, in the first embodiment, because it is possible to automatically obtain the positions of the region of interest without experiencing tracking failures of an extreme level, it is possible to conveniently provide a robust evaluation of the tissue motion.

In the first embodiment described above, to simplify the explanation, the example is explained in which the tracking unit 173 tracks the region of interest in the temporally forward direction. However, the tracking unit 173 may track the region of interest in the temporally backward direction.

In other words, the first estimating unit 173a is able to calculate a motion vector "MvF" in the forward direction from the temporal phase "tk" to the temporal phase "tk+1" and is also able to calculate a motion vector "MvB" in the backward direction from the temporal phase "tk+1" to "tk". In other words, in the first embodiment described above, the first estimating unit 173a estimates the position of the tracking point p(tk+1) in the temporal phase "tk+1" by estimating a motion vector "MvF_P(tk→tk+1)" with respect to the tracking point p(tk) in the temporal phase (tk), based on "MvF".

Instead, the first estimating unit 173a is able to calculate the motion vector "MvB" in the backward direction from the temporal phase "tk+1" to the temporal phase "tk". After that, the first estimating unit 173a is able to estimate a motion vector "MvB_p(tk+1→tk)" with respect to the tracking point p(tk+1) in the temporal phase "tk+1" based on "MvB". As a result, the first estimating unit 173a is able to estimate the position of the tracking point p(tk) at the temporal phase "tk".

In that situation, the defining unit 173b is able to provide information that defines movement quality (i.e., a reliability index) by a combination of "MvF" and "MvB". In other words, the position of p(tk) obtained from "MvB_p(tk+1→tk)" does not necessarily coincide with the position of p(tk) moved to p(tk+1) by "MvF_p(tk→tk+1)". The reason is that "MvF" does not necessarily coincide with "MvB" due to the influence of speckle noise, when mutually-difference pieces of image data are used as search targets in the template matching process. However, if the influence of speckle noise is small, the degree of matching between the two motion vectors is expected to be high.

For this reason, in a modification example where the movement quality (i.e., the reliability index) is defined based on "MvF" and "MvB", the first estimating unit 173a estimates, between the first image data and the second image data, a forward-direction motion vector at each of the tracking points structuring the region of interest from the first temporal phase to the second temporal phase, as well as a backward-direction motion vector at each of the tracking points structuring the region of interest from the second temporal phase to the first temporal phase. After that, the defining unit 173b uses the degree of matching between the forward-direction motion vectors and the backward-direction motion vectors at each of the tracking points structuring the region of interest, as "at least one of the variables obtained from processes performed by the first estimating unit 173a".

In the forward direction from the temporal phase "tk" to "tk+1", the first estimating unit 173a calculates "MvF", estimates "MvF_p(tk→tk+1)", and estimates the position of p(tk+1), by performing the process explained in the embodiment described above. Further, in the backward direction from the temporal phase "tk+1" to "tk", the first estimating unit 173a performs the process explained in the embodiment described above on p(tk+1) determined based on "MvF", in such a manner that the temporal phases are reversed. The first estimating unit 173a thus calculates "MvB" and estimates "MvB_p(tk+1→tk)".

In this situation, both "MvF_p(tk→tk+1)" and "MvB_p(tk+1→tk)" are each considered to be a variable at the tracking point p(tk+1) in the temporal phase "tk+1". In other words, to make generalization, these two variables can be expressed as two variables "MvF_p(t)" and "MvB_p(t)" with respect to the tracking point p(t) at the temporal phase (t). By using these expressions, in one example, the defining unit 173b is able to define a matching degree "MM_p(t)" between the two motion vectors in the forward and the backward directions at the tracking point p(t), by using Formula (7) shown below. In Formula (7), "•" expresses an inner product of the vectors.

$$MM\_p(t) = -MvB\_p(t) \cdot MvF\_p(t) \quad (7)$$

When "MM_p(t)" is defined by using Formula (7), if the inverse vector of the forward-direction motion vector at the tracking point p(t) coincides with the backward-direction motion vector at the tracking point p(t), "MM_p(t)=1" is satisfied. In contrast, according to the definition of Formula (7), if the forward-direction motion vector at the tracking point p(t) is orthogonal to the backward-direction motion vector at the tracking point p(t), "MM_p(t)=0" is satisfied. Further, if the value of "MM_p(t)" is "a positive value smaller than 1", it means that the angle formed by the forward-direction motion vector and the backward-direction motion vector at the tracking point p(t) is in the range larger than 0 degrees and smaller than 90 degrees and that the detected vectors are at least in mutually the same direction. On the contrary, if the value of "MM_p(t)" is "a negative value", it means that the angle formed by the forward-direction motion vector and the backward-direction motion vector at the tracking point p(t) is larger than 90 degrees and that the detected vectors are in opposite directions to each other. Accordingly, it is considered that, while the polarity is also taken into consideration, the smaller the value of "MM_p(t)" is, the lower the movement quality (i.e., the reliability index) is.

Consequently, the defining unit 173b defines a movement quality "Q(s,Mv)" by using "MM_p(t)", while using Formula (8) shown below.

$$\left. \begin{array}{ll} Q(s, Mv) = MM\_p(t) & (MM\_p(t) \geq 0) \\ Q(s, Mv) = 0 & (MM\_p(t) < 0) \end{array} \right\} \quad (8)$$

In other words, the defining unit 173b defines the movement quality "Q(s,Mv)" of each of the remaining motion vectors "Mv" within a segment "s" that contains such a tracking point p(t) of which "MM_p(t)" is equal to or larger than "0", to be "MM_p(t)". In contrast, the defining unit 173b defines the movement quality value "Q(s,Mv)" of each of the remaining motion vectors "Mv" within a segment "s" that contains such a tracking point p(t) of which "MM_p(t)" is a negative value, to be "0". The movement quality defined by using Formula (8) satisfies the condition "0≤Q(s,Mv)≤1". Alternatively, the defining unit 173b may define a movement quality "Q(s,Mv)" by a combination of Formula (5) and Formula (8).

Further, the defining unit 173b defines "Q_P(t)" by using either "Q(s,Mv)" defined by Formula (8) or "Q(s,Mv)" defined by a combination of Formula (5) and Formula (8).

In the description above, the example is explained in which the initial contour position is set in one temporal phase; however, the initial contour position may be set in a plurality of temporal phases. For example, the first embodiment may be configured so that a first initial contour position and a second initial contour position are set in an early diastolic phase and an end systolic phase, during which performing a speckle tracking process is considered to be difficult. In that situation, the tracking unit 173 performs a tracking process that uses the first initial contour position in parallel with a tracking process that uses the second initial contour position.

Further, the processes performed by the second estimating unit 173c are not limited to the first process, the second process, and the third process described above. For example, the second estimating unit 173c may implement an Acoustic Quantification (AQ) method or an Active Shape Model (ASM) method.

In a second embodiment, a control method to reduce the calculation processing amount will be explained. In the first embodiment, the example is explained in which the second position information "Cmodel(t)" is calculated for all of the remaining temporal phases. However, to automatically detect an accurate position of the region of interest (the contour) in a stable manner regardless of the image quality, the calculation amount increases if the second position information is calculated for all of the remaining temporal phases. In particular, the first process in which "Cdict(t)" is estimated by the discriminator requires time for the discriminator to perform the discriminating process, although the accuracy in the contour position estimation is enhanced.

Incidentally, during the speckle tracking process, the region of interest (the contour) is determined by using the first position information "Cvector(t)" in most situations. Only when the movement quality (i.e., the reliability index) is degraded, "Cmodel(t)" is necessary. For this reason, in the second embodiment, an example will be explained in which the calculation time is reduced by calculating "Cmodel(t)" only for such temporal phases in which the movement quality is degraded.

An ultrasound diagnostic apparatus according to the second embodiment has the same configuration as that of the ultrasound diagnostic apparatus according to the first embodiment illustrated in FIG. 1. Further, the tracking unit 173 according to the second embodiment has the same configuration as that of the tracking unit 173 according to the first embodiment illustrated in FIG. 4.

It should be noted, however, that the tracking unit 173 according to the second embodiment performs processes explained below under the control of the controlling unit 18. Specifically, the tracking unit 173 according to the second embodiment outputs the first position information as the position information of the region of interest, for such a temporal phase in which an average value of the reliability indices (the movement quality) in the region of interest is equal to or larger than a predetermined threshold value. In contrast, the tracking unit 173 according to the second embodiment outputs position information resulting from combining the first position information with the second position information as the position information of the region of interest, for such a temporal phase in which the average value is smaller than the predetermined threshold value.

In the following sections, a process performed in the second embodiment when the first image data is "I(t1)" and the second image data is "I(t2)" will be explained. In the second embodiment also, the processes by the obtaining unit 171 and the setting unit 172 are performed in the same manner as in the first embodiment. After that, by performing the process explained in the first embodiment, the first estimating unit 173a estimates the first position information "Cvector(t)" in "I(t2)". Further, by performing the process explained in the first embodiment, the defining unit 173b defines the movement quality "Q_p(t2)" at each of the points "p(t2)" structuring "Cvector(t)".

After that, the defining unit 173b calculates "Q(t2)" by averaging the movement quality "Q_p(t)" at the points "p(t2)".

The controlling unit 18 obtains the value "Q(t2)" from the defining unit 173b and compares "Q(t2)" with a quality threshold value "Qth". For example, "Qth" may be stored in the internal storage unit 16 in advance. Alternatively, "Qth" may be set by the operator, for example.

After that, if "Q(t2)≥Qth" is satisfied, the controlling unit 18 stops the processes performed by the second estimating unit 173c and the combining unit 173d and determines "Cvector(t2)" estimated by the first estimating unit 173a to be "C(t2)". The first estimating unit 173a outputs "Cvector (t2)" as "C(t2)" to the motion information calculating unit 174.

On the contrary, if "Q(t2)<Qth" is satisfied, the controlling unit 18 causes the second estimating unit 173c and the combining unit 173d to start the processes. As a result, the second estimating unit 173c estimates "Cmodel(t2)", whereas the combining unit 173d obtains "Cmodel(t2)'" from "Cvector(t2)" and "Cmodel(t2)". After that, the combining unit 173d obtains "C(t2)" by performing a weighted addition on "Cvector(t2)" and "Cmodel(t2)'" based on "Q_p (t2)" and outputs "C(t2)" to the motion information calculating unit 174.

The explanation in the first embodiment is applicable to the second embodiment, except for the process of judging whether the processes by the second estimating unit 173c and the combining unit 173d should be performed based on the average value.

Figure 19:
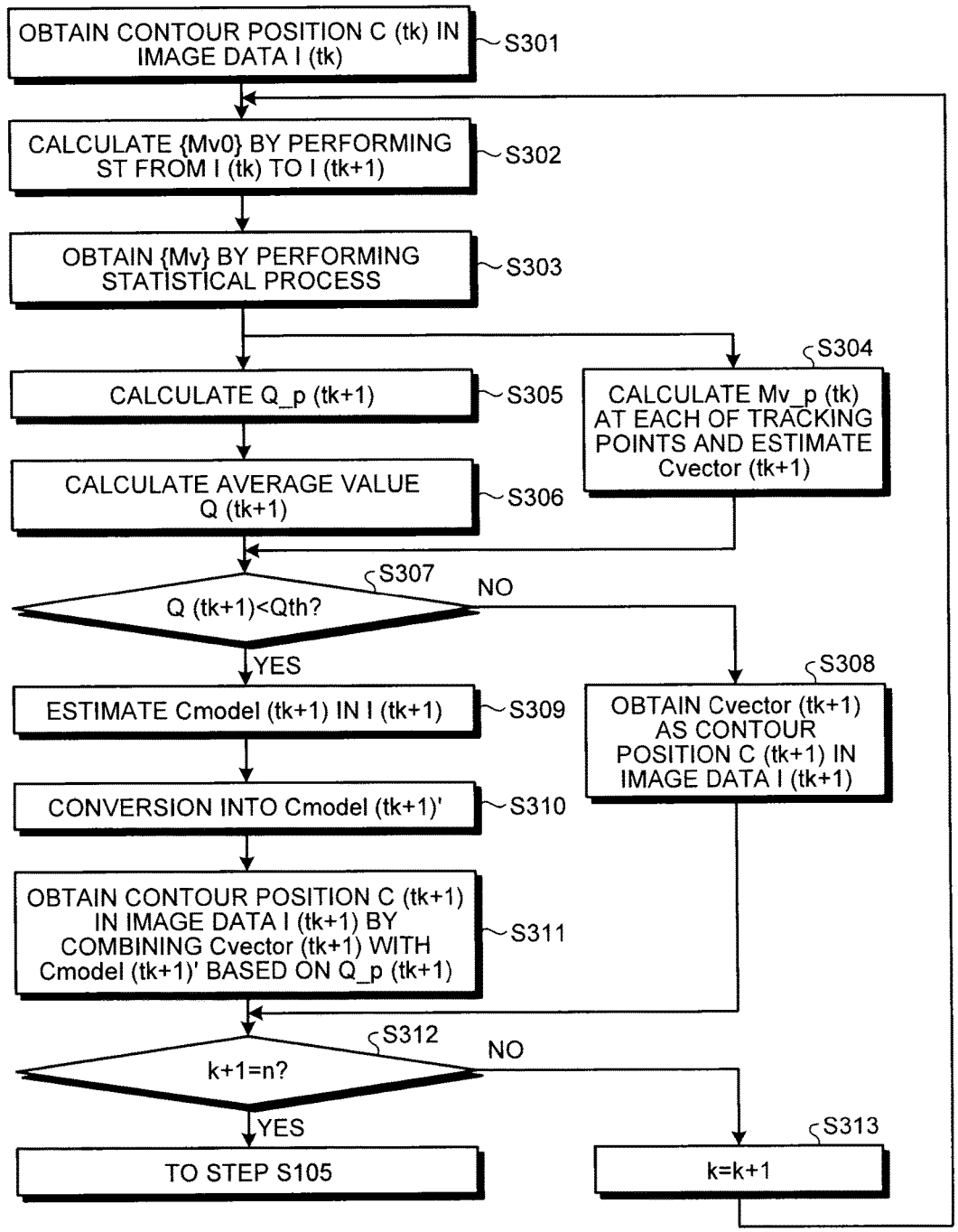
FIG. 19 is a flowchart for explaining exemplary processes performed by a tracking unit according to a second embodiment.

Next, processes performed by the ultrasound diagnostic apparatus according to the second embodiment will be explained, with reference to FIG. 19. FIG. 19 is a flowchart for explaining exemplary processes performed by the tracking unit according to the second embodiment.

Specifically, the process at step S104 in FIG. 17 is realized as the process in the flowchart in FIG. 19, in the second embodiment. In other words, the first estimating unit 173a obtains a contour position C(tk) in the image data I(tk) (step S301). In the process for the first time, "tk=t1" is satisfied.

After that, the first estimating unit 173a calculates {Mv0} by performing a speckle tracking (ST) process from I(tk) to I(tk+1) (step S302). Subsequently, the first estimating unit 173a obtains a group of remaining motion vectors {Mv}, by performing a statistical process (step S303). The first estimating unit 173a then calculates Mv_p(tk) at each of the tracking points by using {Mv} and estimates Cvector(tk+1) (step S304).

Further, while the process at step S304 is being performed, the defining unit 173b calculates a movement quality Q_p(tk+1) at each of the tracking points p(tk+1) structuring Cvector(tk+1) (step S305). After that, the defining unit 173b calculates an average value Q(tk+1) of the movement qualities Q_p(tk+1) at the tracking points p(tk+1) (step S306).

Subsequently, the controlling unit 18 judges whether Q(tk+1) is smaller than Qth (step S307). If Q(tk+1) is equal to or larger than Qth (step S307: No), the tracking unit 173 obtains Cvector(tk+1) as the contour position C(tk+1) in the image data I(tk+1) (step S308).

On the contrary, if Q(tk+1) is smaller than Qth (step S307: Yes), the second estimating unit 173c estimates Cmodel(tk+ 1) in I(tk+1) (step S309).

After that, the combining unit 173d converts Cmodel(tk+ 1) into Cmodel (tk+1)', by using Cvector(tk+1) (step S310). Subsequently, the combining unit 173d obtains a contour position C(tk+1) in I(tk+1) by combining Cvector(tk+1) with Cmodel(tk+1)' based on the movement quality Q_p (tk+1) at each of the tracking points p(tk+1) (step S311).

After the process at step S308 or step S311 has been performed, the combining unit 173*d* judges whether "k+1=n" is satisfied (step S312). If "k+1<n" is satisfied (step S312: No), the combining unit 173*d* determines that there are one or more temporal phases for which the contour tracking process has not yet been performed and sets k so as to satisfy "k=k+1" (step S313). Further, by using C(tk+1) as C(tk), the tracking unit 173 repeats the processes at step S302 and thereafter.

On the contrary, if "k+1=n" is satisfied (step S312: Yes), the combining unit 173*d* informs the motion information calculating unit 174 that the contour tracking process has been finished for all the temporal phases, so that the motion information calculating unit 174 starts the process at step S105.

As explained above, according to the second embodiment, if the quality (the reliability) of the movement information is high, the processes performed by the second estimating unit 173*c* and the combining unit 173*d* are omitted. Consequently, it is possible to accurately and efficiently obtain the tracking result of the region of interest.

Figure 20:
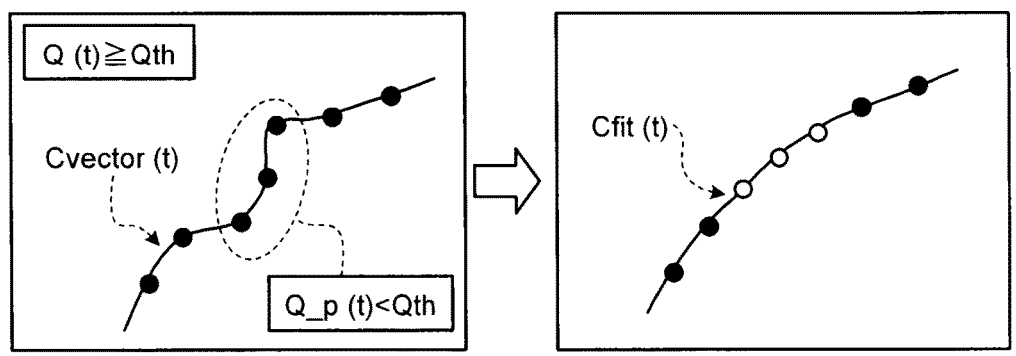
FIG. 20 is a drawing for explaining a modification example of the second embodiment.

The second embodiment may also be executed in a modification example described below. FIG. 20 is a drawing for explaining the modification example of the second embodiment. The situations in which "Q(t)≥Qth" is satisfied can roughly be divided into a first situation in which all the movement quality "Q_p(t)" are equal to or larger than "Qth" and a second situation in which some of the movement quality "Q_p(t)" are locally smaller than "Qth". In the first situation, the tracking unit 173 determines Cvector(t) to be the contour position C(t) in the image data I(t).

Figure 13C:
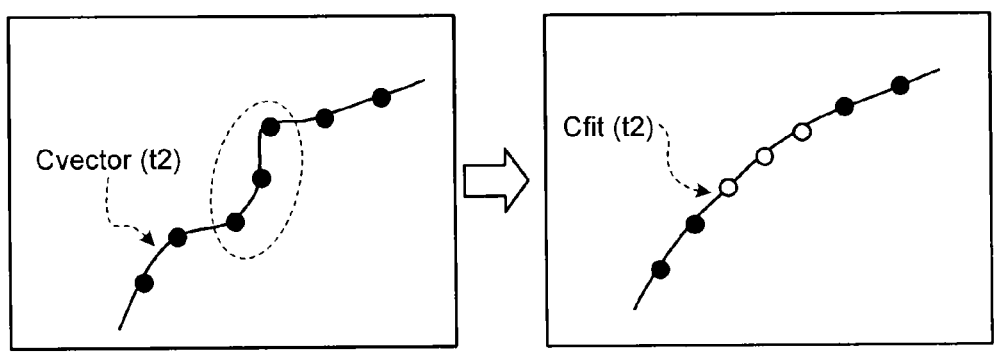

On the contrary, in the second situation, i.e., there are one or more points at which "Q_p(t)<Qth" is satisfied locally, although "Q(t)≥Qth" is generally satisfied (see inside the dotted circle in the left section of FIG. 20), the second estimating unit 173*c* performs the third process explained with reference to FIG. 13C, according to an instruction from the controlling unit 18. In other words, as illustrated in the right section of FIG. 20, the second estimating unit 173*c* estimates "Cfit(t)" in "I(t)" by interpolating the contour inside the dotted circle by performing a least squares fitting process that uses the points in the surroundings that have higher movement quality. After that, the second estimating unit 173*c* outputs "Cfit(t)" as "Cmodel(t)" to the combining unit 173*d*.

The calculation amount in the third process is smaller than that in the first process or the second process. Thus, by implementing the modification example described above, it is possible to avoid using Cvector(t), which as a whole has high reliability, but locally has low reliability, as C(t), and quickly obtain "C(t)" having high reliability.

In the first and the second embodiments described above, the example is explained in which the initial contour is manually set by the operator; however, the initial contour may be set by implementing the method described above by which a contour position is estimated based on information other than the movement information. In other words, in the first and the second embodiments, the setting unit 172 may set the initial contour based on various types of processes performed by the second estimating unit 173*c*. With this configuration, an accurate tracking process of the region of interest can be further automated, so that the operator is able to analyze the tissue motion more conveniently. When the initial contour is automatically set, it is desirable to have a configuration in which a procedure of correcting the initial contour position can be received from the operator.

Further, when the initial contour is automatically set, it is possible to implement the image processing methods explained in the first and the second embodiments in a substantially real-time manner with the acquisition of the moving image data. In other words, by sequentially implementing any of the image processing methods explained in the first and the second embodiments while acquiring the moving image data, the ultrasound diagnostic apparatuses according to the first and the second embodiments are able to provide a tissue motion analyzing method that has stable reliability in a substantially real-time manner.

Further, in the first and the second embodiments, the example is explained in which the tracking process is performed on the two-dimensional moving image data taken on the one cross-sectional plane; however, the image processing methods explained in the first and the second embodiments are applicable to a situation where the tracking process is performed on a plurality of pieces of two-dimensional moving image data taken on a plurality of cross-sectional planes. Further, as mentioned above, the image processing methods explained in the first and the second embodiments are applicable to a situation where the tracking process is performed on three-dimensional moving image data.

Further, the organ to which the image processing methods described above are applied is not limited to the heart. The organ may be an arterial vessel (e.g., a carotid artery) that repeatedly expands and contracts in synchronization with cardiac cycles. Further, the image processing methods described above may be applied to a tissue in motion such as "a soft tissue like the liver or the thyroid gland" or "a muscle", for the purpose of understanding the firmness or the dynamics of the tissue through an analysis of a movement index related to strains or displacements.

Further, the image processing methods described above may be applied to two- or three-dimensional moving image data of medical image data in which it is possible to track a region of interest by performing a template matching process, such as X-ray diagnostic apparatuses, X-ray CT apparatuses, and MRI apparatuses. In other words, the image processing methods explained in the first and the second embodiments may be implemented by a medical image diagnostic apparatus other than the ultrasound diagnostic apparatus. Further, the image processing methods described above may be implemented by an image processing apparatus that is installed independently of the medical image diagnostic apparatus.

The constituent elements of the apparatuses that are illustrated in the drawings in the exemplary embodiments and the modification examples described above are based on functional concepts. Thus, it is not necessary to physically configure the elements as indicated in the drawings. In other words, the specific mode of distribution and integration of the apparatuses is not limited to the ones illustrated in the drawings. It is acceptable to functionally or physically distribute or integrate all or a part of the apparatuses in any arbitrary units, depending on various loads and the status of use. Further, all or an arbitrary part of the processing functions performed by the apparatuses may be realized by a CPU and a computer program that is analyzed and executed by the CPU or may be realized as hardware using wired logic.

Furthermore, the image processing methods explained in the exemplary embodiments and the modification examples above may be realized by causing a computer such as a personal computer or a workstation to execute an image processing computer program (hereinafter, an "image processing program") that is prepared in advance. The image processing program may be distributed via a network such as the Internet. Further, it is also possible to record the image processing program onto a computer-readable recording medium such as a hard disk, a flexible disk (FD), a Compact Disk Read-Only Memory (CD-ROM), a Magneto-optical (MO) disk, or a Digital Versatile Disk (DVD), so that a computer is able to read the image processing program from the recording medium and to execute the read image processing program.

As explained above, according to at least one aspect of the embodiments and the modification examples, it is possible to accurately obtain the tracking result of the region of interest.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnostic apparatus comprising:
an ultrasound probe configured to emit ultrasound waves and detect reflected waves that are used to generate ultrasound image data, the ultrasound image data representing two- or three-dimensional ultrasound images of a target-including region containing a tissue in motion, the ultrasound images corresponding to a plurality of temporal phases; and
processing circuitry configured to
set, for at least one temporal phase of the plurality of temporal phases, a two- or three-dimensional region of interest in the ultrasound image data, the region of interest representing a portion of the tissue,
obtain movement information by a tracking process using the ultrasound images, wherein the movement information represents motion vectors of first points in the region of interest, and corresponds to a likelihood that when a first point is translated according to the motion vectors relative to positions within the respective ultrasound images, the positions within the respective ultrasound images refer to a same location on the target,
obtain a reliability index based on indicia of reliability of the movement information including at least one variable obtained from the tracking process,
determine, using the movement information, movement-based positions, which are first estimates of positions of the region of interest in ultrasound images corresponding to remaining temporal phases, which are temporal phases of the plurality of temporal phases other than the at least one temporal phase,
determine, using shape information of a shape of the tissue, shape-based positions, which are second estimates of the positions of the region of interest in the ultrasound images corresponding to the remaining temporal phases, the shape-based positions being determined by estimating the shape of the tissue in the remaining temporal phases and then determining the second estimates of the positions of the region of interest from the estimated shape of the tissue in the remaining temporal phases,
combine the movement-based positions with the shape-based positions by weighting the movement-based positions relative to the shape-based positions based on the reliability index, to generate position information of the region of interest, the weighting being performed such that, for a value of the reliability index indicating a greater reliability of the movement information, a contribution to the generated position information by the movement-based positions is increased relative to a contribution by the shape-based positions, and
track the region of interest using the position information of the region of interest by updating the region of interest with respect to time in accordance with changes of the region of interest represented by the position information.

2. The ultrasound diagnostic apparatus according to claim 1, wherein the plurality of temporal phases correspond to a time period of at least one cyclic period and the ultrasound images were acquired when the tissue was in periodic motion.

3. The ultrasound diagnostic apparatus according to claim 1, wherein the processing circuitry is configured to
estimate the movement information between a first image of the ultrasound image data corresponding to a first temporal phase of the plurality of temporal phases and a second image of the ultrasound image data corresponding to a second temporal phase of the plurality of temporal phases, which is temporally adjacent to the first temporal phase,
estimate the movement-based positions in the second image by moving the region of interest in the first image based on the estimated movement information, and
estimate the shape-based positions in the second image.

4. The ultrasound diagnostic apparatus according to claim 3, wherein the processing circuitry is configured to
estimate the movement-based positions by calculating motion vectors at second points in a region that contains the region of interest, selecting the first points to be tracking points structuring the region of interest, eliminating statistically-abnormal motion vectors from the calculated motion vectors to generate remaining motion vectors, and estimating the motion vectors at the first points using the group of remaining motion vectors, and
define the reliability index based on said at least one variable, wherein said at least one variable is one or more of a density of the remaining motion vectors in vicinal regions of the first points and a variance of motion vectors at the first points in vicinal regions of the first points.

5. The ultrasound diagnostic apparatus according to claim 3, wherein the processing circuitry is configured to
estimate, for each of the first points, which are tracking points structuring the region of interest, and for a time interval between the first image and the second image, forward-direction motion vectors representing motions forward in time from the first temporal phase to the second temporal phase, as well as backward-direction motion vectors representing motions backward in time from the second temporal phase to the first temporal phase, and
define the reliability index based on said at least one variable, wherein said at least one variable includes a degree of matching between the forward-direction motion vector and the backward-direction motion vector at respective first points.

6. The ultrasound diagnostic apparatus according to claim 3, wherein the processing circuitry is configured to
   calculate motion vectors at second points in a region that contains the region of interest by performing a template matching process, and
   define the reliability index based on said at least one variable, wherein said at least one variable includes one or more of a level of similarity between templates used in the template matching process, a signal variance value of a standard template used in the template matching process, and an average signal value of the standard template.

7. The ultrasound diagnostic apparatus according to claim 3, wherein the processing circuitry is configured to estimate the shape-based positions by using one or more of comparing a shape of the shape-based positions of the second image with shape dictionary information corresponding to a same temporal phase as the second image; minimizing a shape energy of the shape of the shape-based positions of the second image; and fitting the shape of the shape-based positions of the second image using a least square method.

8. The ultrasound diagnostic apparatus according to claim 3, wherein the processing circuitry is configured to perform the combining of the movement-based positions with the shape-based positions using a weighted addition of the movement-based positions and the shape-based positions in such a manner that a larger weight is applied to estimates of the positions of the region of interest of the movement-based positions corresponding to first points for which the reliability index indicates greater reliability.

9. The ultrasound diagnostic apparatus according to claim 1, further comprising:
   controlling circuitry configured to, for a temporal phase of the plurality of temporal phases,
      cause the processing circuitry to output the movement-based positions as the position information of the region of interest when an average of values of the reliability index corresponding to the region of interest and the temporal phase is equal to or larger than a predetermined threshold value, and
      cause the processing circuitry to output the position information resulting from combining the movement-based positions with the shape-based positions as the position information of the region of interest when the average is smaller than the predetermined threshold value.

10. The ultrasound diagnostic apparatus according to claim 7, wherein the processing circuitry is configured to, for a temporal phase of the plurality of temporal phases,
   determine the shape-based positions by comparing the shape of the shape-based positions with the shape dictionary information when the shape dictionary information exists for the temporal phase, and
   determine the shape-based positions by either minimizing the shape energy of the shape of the shape-based positions or fitting the shape of the shape-based positions using a least square method when the shape dictionary information exists for the temporal phase.

11. The ultrasound diagnostic apparatus according to claim 7, wherein the processing circuitry is configured to determine the shape-based positions by fitting the shape of the shape-based positions using a least square method at a site in the region of interest corresponding to a point of the first points for which the reliability index indicates reliability is poor.

12. The ultrasound diagnostic apparatus according to claim 1, further comprising
   controlling circuitry configured to cause a display to display motion of the tissue, wherein
   the processing circuitry is configured to calculate the motion of the tissue using the position information of the region of interest in each of the ultrasound images.

13. An image processing apparatus comprising: processing circuitry configured to
   obtain ultrasound image data representing two- or three-dimensional ultrasound images of a target-including region containing a tissue in motion, the ultrasound images corresponding to a plurality of temporal phases,
   set, for at least one temporal phase of the plurality of temporal phases, a two- or three-dimensional region of interest in the ultrasound image data, the region of interest representing a portion of the tissue,
   obtain movement information by a tracking process using the ultrasound images, wherein the movement information represents motion vectors of first points in the region of interest, and corresponds to a likelihood that when a first point is translated according to the motion vectors relative to positions within the respective ultrasound images, the positions within the respective ultrasound images refer to a same location on the target,
   obtain a reliability index based on indicia of reliability of the movement information including at least one variable obtained from the tracking process,
   determine, using the movement information, movement-based positions, which are first estimates of positions of the region of interest in ultrasound images corresponding to remaining temporal phases, which are temporal phases of the plurality of temporal phases other than the at least one temporal phase,
   determine, using shape information of a shape of the tissue, shape-based positions, which are second estimates of the positions of the region of interest in the ultrasound images corresponding to the remaining temporal phases, the shape-based positions being determined by estimating the shape of the tissue in the remaining temporal phases and then determining the second estimates of the positions of the region of interest from the estimated shape of the tissue in the remaining temporal phases,
   combine the movement-based positions with the shape-based positions by weighting the movement-based positions relative to the shape-based positions based on the reliability index, to generate position information of the region of interest, the weighting being performed such that, for a value of the reliability index indicating a greater reliability of the movement information, a contribution to the generated position information by the movement-based positions is increased relative to a contribution by the shape-based positions, and
   track the region of interest using the position information of the region of interest by updating the region of interest with respect to time in accordance with changes of the region of interest represented by the position information.

14. An image processing method performed by processing circuitry, the method comprising:
   obtaining ultrasound image data representing two- or three-dimensional ultrasound images of a target-including region containing a tissue in motion, the ultrasound images corresponding to a plurality of temporal phases setting, for at least one temporal phase of the plurality of temporal phases, a two- or three-dimensional region of interest in the ultrasound image data, the region of interest representing a portion of the tissue;

obtaining movement information by a tracking process using the ultrasound images, wherein the movement information represents motion vectors of first points in the region of, and corresponds to a likelihood that when a first point is translated according to the motion vectors relative to positions within the respective ultrasound images, the positions within the respective ultrasound images refer to a same location on the target, obtaining a reliability index based on indicia of reliability of the movement information including at least one variable obtained from the tracking process, determining, using the movement information, movement-based positions, which are first estimates of positions of the region of interest in ultrasound images corresponding to remaining temporal phases, which are temporal phases of the plurality of temporal phases other than the at least one temporal phase, determining, using shape information of a shape of the tissue, shape-based positions, which are second estimates of the positions of the region of interest in the ultrasound images corresponding to the remaining temporal phases, the shape-based positions being determined by estimating the shape of the tissue in the remaining temporal phases and then determining the second estimates of the positions of the region of interest from the estimated shape of the tissue in the remaining temporal phases;

combining the movement-based positions with the shape-based positions by weighting the movement-based positions relative to the shape-based positions based on the reliability index, to generate position information of the region of interest, the weighting 44e being performed such that, for a value of the reliability index indicating a greater reliability of the movement information, a contribution to the generated position information by the movement-based positions is increased relative to a contribution by the shape-based positions, and tracking the region of interest using the position information of the region of interest by updating the region of interest with respect to time in accordance with changes of the region of interest represented by the position information.

\* \* \* \* \*